United States Patent [19]
Allen et al.

[11] Patent Number: 5,620,689
[45] Date of Patent: Apr. 15, 1997

[54] LIPOSOMES FOR TREATMENT OF B-CELL AND T-CELL DISORDERS

[75] Inventors: Theresa M. Allen, Edmonton, Canada; Francis J. Martin, San Francisco, Calif.

[73] Assignee: Sequus Pharmaceuuticals, Inc., Menlo Park, Calif.

[21] Appl. No.: 475,050

[22] Filed: Jun. 7, 1995

Related U.S. Application Data

[63] Continuation-in-part of Ser. No. 40,544, Mar. 31, 1993, Pat. No. 5,527,528, which is a continuation-in-part of Ser. No. 642,321, Nov. 15, 1991, Pat. No. 5,213,804, which is a continuation-in-part of Ser. No. 425,224, Oct. 10, 1989, Pat. No. 5,013,556.

[51] Int. Cl.$^6$ .................. A61K 51/12; A61K 39/44; A61K 9/127; C07K 17/00
[52] U.S. Cl. .................. 424/178.1; 424/181.1; 424/450; 424/812; 424/180.1; 530/391.7
[58] Field of Search .................. 424/178.1, 181, 424/450, 812; 530/391.7

[56] References Cited

U.S. PATENT DOCUMENTS

| | | |
|---|---|---|
| 4,732,863 | 3/1988 | Tomasi et al. |
| 4,863,713 | 9/1989 | Goodwin et al. |
| 4,885,172 | 12/1989 | Bally et al |
| 4,898,735 | 2/1990 | Barenholz et al. |
| 4,948,590 | 8/1990 | Hawrot et al |
| 5,013,556 | 5/1991 | Woodle et al. |
| 5,527,528 | 6/1996 | Allen et al. ............ 424/178.1 |

OTHER PUBLICATIONS

Abuchowski, A., et al., "Effect of Covalent Attachment of Polyethylene Glycol on Immunogenicity and Circulating Life of Bovine Liver Catalase," *J. Biol. Chem.* 252(11):3582 (1977).

Ding, L., et al., "Effective Drug–Antibody Targeting Using a Novel Monoclonal Antibody Against the Proliferative Compartment of Mammalian Squamouse Carcinomas," *Cancer Immunol. Immunother.* 31:105–109 (1990).

Hnathowich, D. J., et al., "Investigations of Avidin and Biotin for Imaging Applications," *J. Nucl. Med.* 28:129–1302 (1987).

Klibanov, A.L., and Huang, L., "Long–Circulating Liposomes: Development and Perspectives," *J. Liposome Res.* 2(3):321–334 (1992).

McQuarrie, S.A., et al., "A Pharmacokinetic Comparison of Murine and Chimeric Forms of the $^{99m}$Tc Labelled 174H.64 Monoclonal Antibody," *JNM & Biol.*

*Primary Examiner*—Frank C. Eisenschenk
*Attorney, Agent, or Firm*—Peter J. Dehlinger; Judy M. Mohr

[57] ABSTRACT

A method of treating a subject having a disorder characterized by a neoplasm of B-lymphocyte or T-lymphocyte lineage cells is described. The method includes administering a suspension of liposomes having a surface coating of polyethylene glycol chains. Attached to the distal ends of the chains are antibodies or antibody fragments effective to bind to an antigen specific to the affected cells. In one embodiment, anti-CD19 antibodies are attached to the liposome-bound chains, for treatment of multiple myeloma.

19 Claims, 16 Drawing Sheets

I
$NH_2-CH_2-CH_2(CH_2CH_2O)_nCH_2CH_2NH_2$
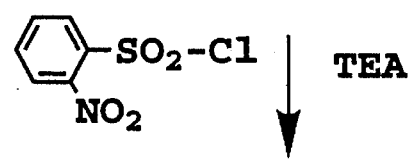 | TEA
II
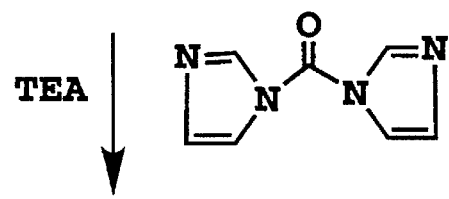 TEA
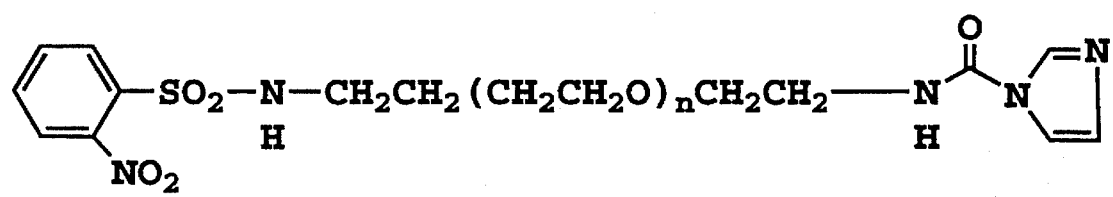
III
↓ TEA, DSPE
↓ ACIDOLYSIS
Fig. 2A

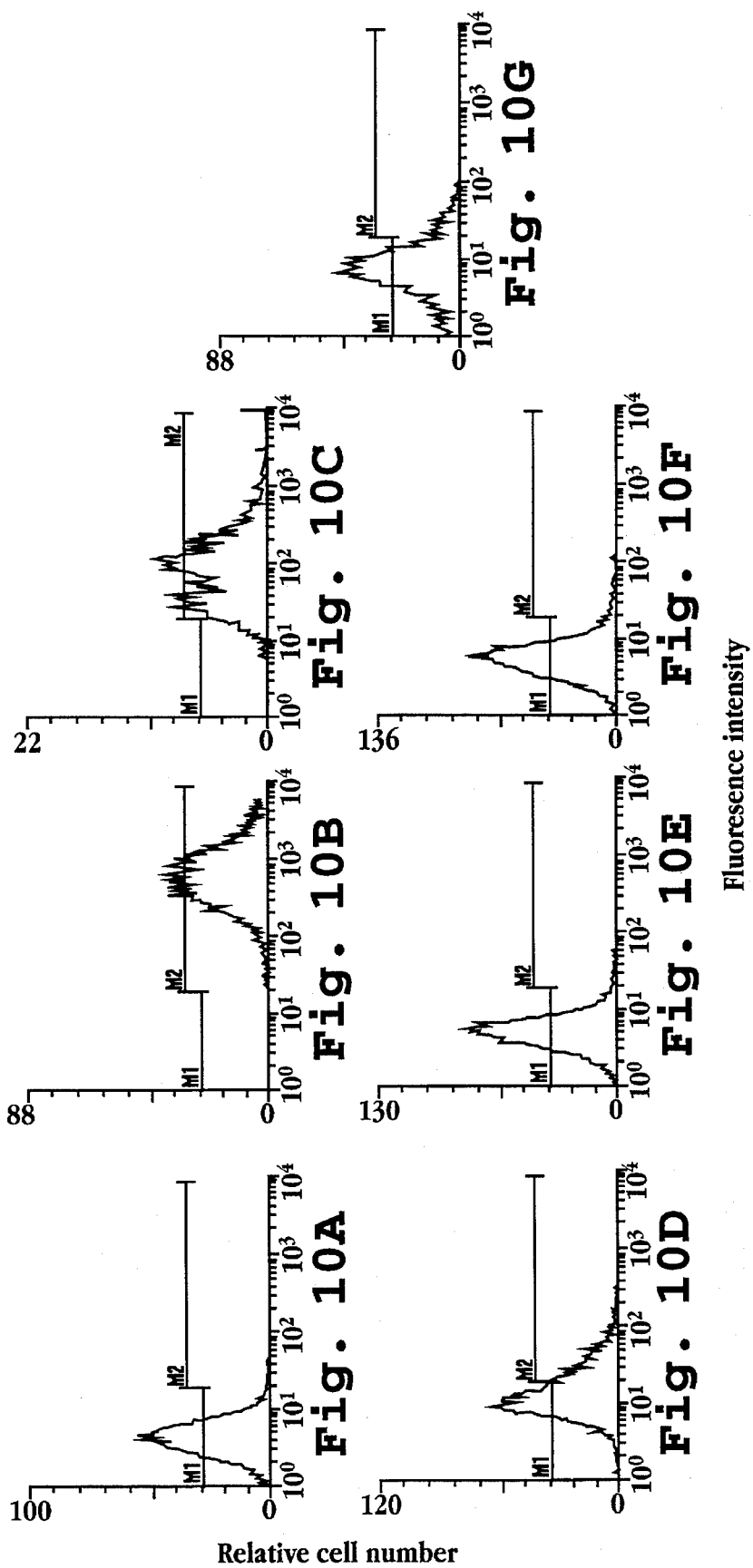

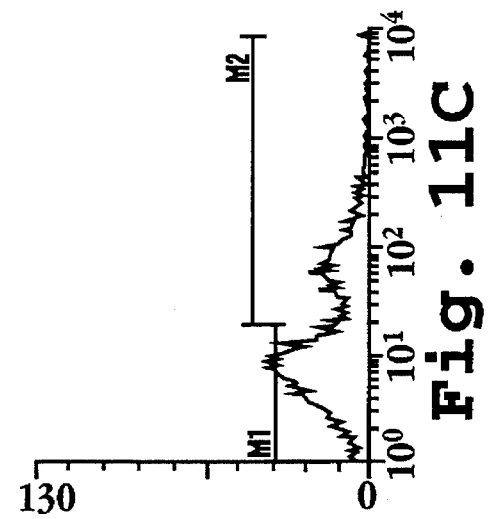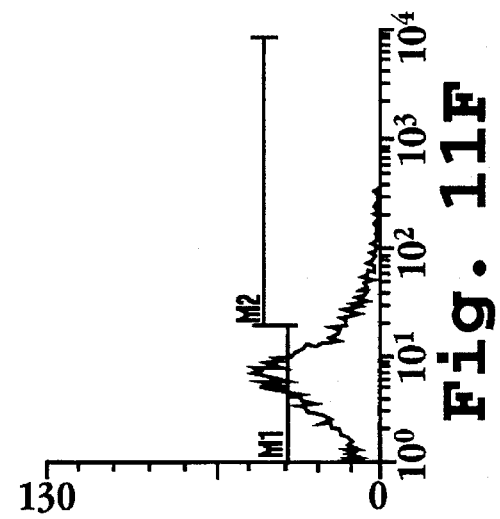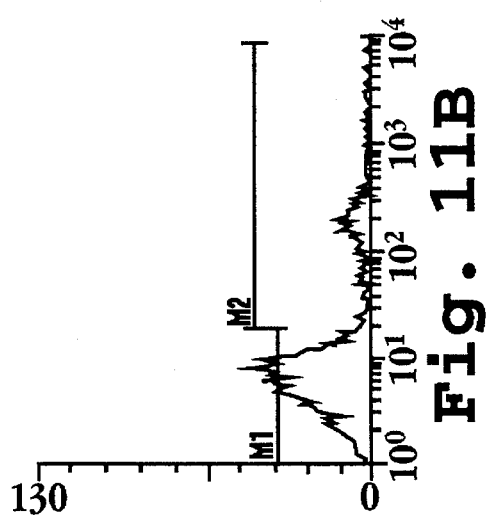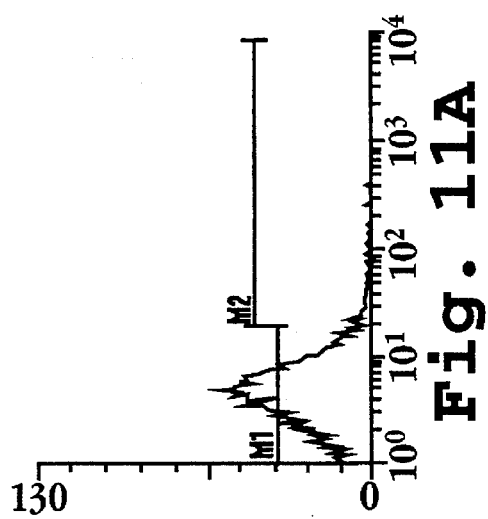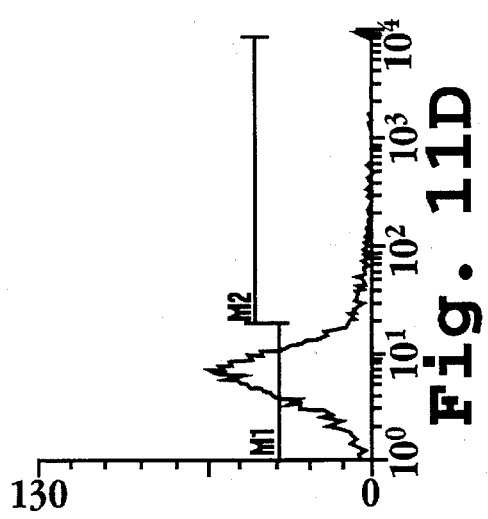

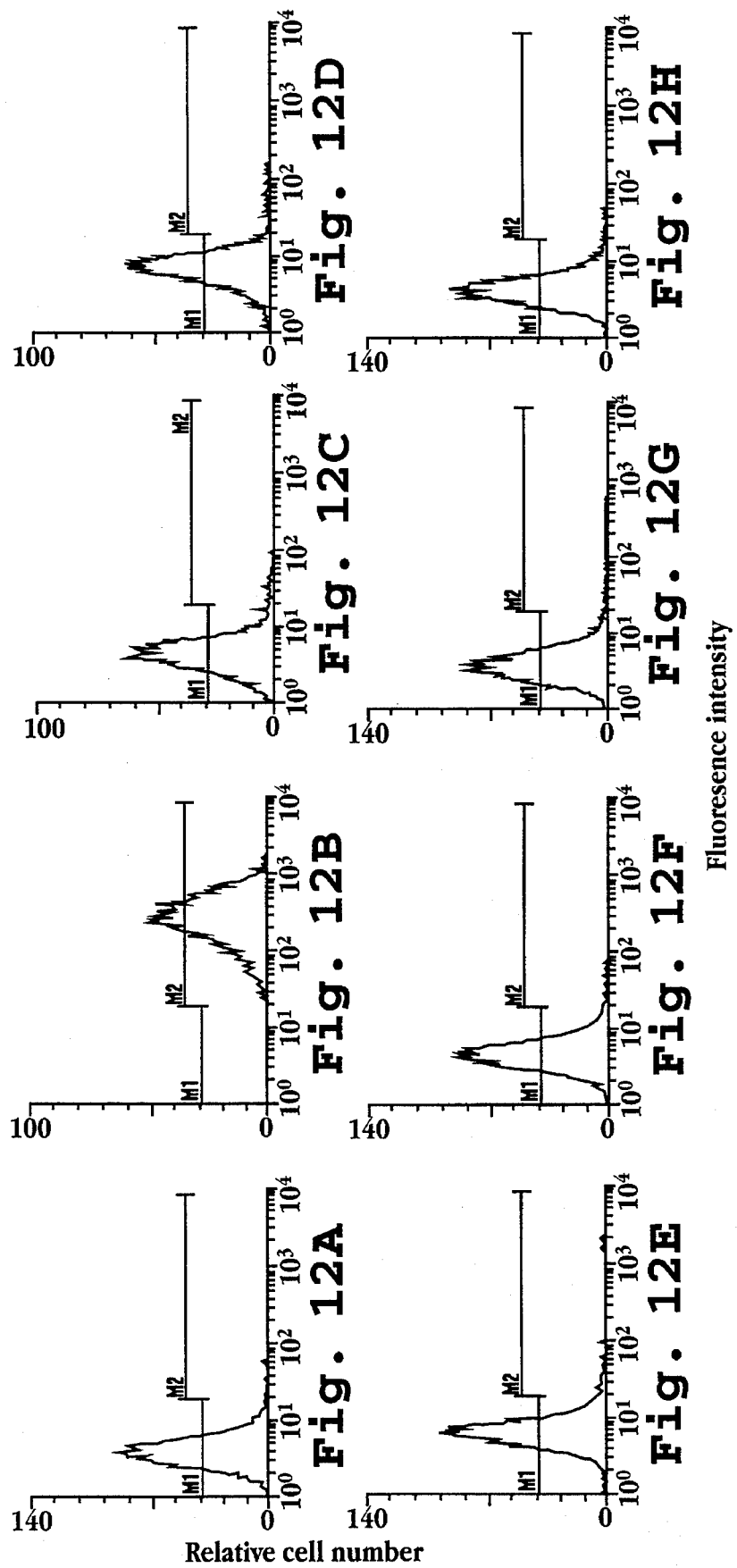

LIPOSOMES FOR TREATMENT OF B-CELL AND T-CELL DISORDERS

The present invention is a continuation-in-part of Ser. No. 08/040,544, now U.S. Pat. No. 5,527,528, filed Mar. 31, 1993, which in turn is a continuation-in-part of Ser. No. 07/642,371, now U.S. Pat. No. 5,213,804, filed Jan. 15, 1991, which in turn is a continuation-in-part of Ser. No. 07/425,224, now U.S. Pat. No. 5,013,556, filed Oct. 20, 1989.

FIELD OF THE INVENTION

The present invention relates to a method of treating disorders derived from B-lymphocyte or T-lymphocyte lineage cells by administering liposomes having an encapsulated agent and attached antibodies for specific binding to the affected B-cells or T-cells.

REFERENCES

Harrison's "Principles of Internal Medicine", 12th Edition, J. D. Wilson et al., Eds. McGraw-Hill, New York (1991).
Mabrey, S., et al., (1978) Biochem. 17:2464–2468.
Mayer, L. D., et al., (1986) Biochim. Biophys. Acta 857:123–126.
Mayer, L. D., et al., (1989) Canc. Res. 49:5922–5930.
Martin, F. J. (1990) In: *Specialized Drug Delivery Systems-Manufacturing and Production Technology*, (P. Tyle, ed.) Marcel Dekker, New York, pp. 267–316.
Martin, F. J., et al., (1993) U.S. Pat. No. 5,213,804.
Olson, F., et al., (1979) Biochim. Biophys. Acta 557:9–23.
Pilarski, L., Onc. Clin. of America, 6:297 (1993).
Szoka, F., Jr., et al. (1980) Ann. Rev. Biophys. Bioeng. 9:467.
Tsong, T. Y. (1975) Biochem. 14:5409–5414, 54157.
Zalipsky, S., et al., Polymer Preprints 27(1): 1 (1986).
Zalipsky, S., et al., (1987) Int. J. Peptide Res. 30:740.
Zalipsky, S., et al., (1990) J. Bioactive Compat. Polym. 5:227.
Zalipsky, S., et al., (1992a) Poly (Ethylene Glycol)Chemistry: Biotechnical and Biomedical Applications (J. M. Harris, ed.) Plenum Press, pg. 347–370.
Zalipsky, S., et al., (1992b) Biotechnol. Appl. Biochem. 15:100.

BACKGROUND OF THE INVENTION

The plasma cell disorders are monoclonal neoplasms related to one another by virtue of their development from common progenitors in the B-lymphocyte lineage. Included in this group of plasma cell disorders are multiple myeloma, Waldenstrom's macroglobulinemia, and primary amyloidosis (Harrison).

Under normal circumstances, maturation to antibody-secreting plasma cells is stimulated by exposure to the antigen for which the surface immunoglobulin is specific. However, in the plasma cell disorders the control over this process is lost.

Multiple myeloma represents a malignant proliferation of plasma cells. The disease results from the uncontrolled proliferation of plasma cells derived from a single clone. The tumor, its products, and the host response to it result in a number of organ dysfunctions and symptoms of bone pain or fracture, renal failure, susceptibility to infection, anemia, and other symptoms.

The vast majority of patients with myeloma require therapeutic intervention, and chemotherapy is one common therapy. Conventional chemotherapy can be effective against the malignant plasma cells in the bone marrow, but is often ineffective in killing the regenerative blood-borne B cells which are responsible for patient relapse, as the malignant B cell population often become multidrug resistant, making treatment difficult. It has recently been shown that the malignant B cell population is responsible for repopulating the bone marrow and causing patient death (Pilarski).

The leukemias are a heterogeneous group of neoplasms arising from the malignant transformation of hematopoietic cells. Leukemic cells proliferate primarily in the bone marrow and lymphoid tissues where they interfere with normal hematopoiesis and immunity. Ultimately they emigrate into the peripheral blood and infiltrate other tissues (Harrison).

Leukemias are classified according to the cell types primarily involved, myeloid or lymphoid, and as acute or chronic based upon the natural history of the disease. Acute leukemias have a rapid clinical course, resulting in death within a matter of months without effective treatment.

Acute lymphocytic leukemia is one example, where approximately 60 percent of acute lymphocytic leukemia cases are common acute lymphocytic leukemia, where the cells are Tdt-positive and have the common acute lymphocytic leukemia antigen but do not express surface membrane immunoglobulin or T-cell antigens. These cells are usually derived from precursors of the B-cell lineage.

About 20 percent of acute lymphocytic cases are of the T-cell type, where the T-lymphoblasts express the E-rosette receptor or other T-lymphocyte related antigens. T-cell acute lymphocytic leukemia usually occurs in adolescent males and is associated by a high leukocyte count and an anterior mediastinal mass.

The malignant lymphomas, in contrast to leukemias, are neoplastic transformation of cells that reside predominately in lymphoid tissues. Non-Hodgkin's lymphomas are derived from both B-cell and T-cell origins (Harrison), where 90% of all cases of non-Hodgkin's lymphomas are of B-cell derivation and the remaining 10% are of T-cell derivation.

SUMMARY OF THE INVENTION

In one aspect, the invention includes a method of treating a subject having a disorder characterized by a neoplasm of B-lymphocyte lineage cells or T-lymphocyte lineage cells. The method includes administering to the subject, a suspension of liposomes having a surface coating of polyethylene glycol chains effective to increase the blood circulation lifetime of the liposomes severalfold over that of liposomes in the absence of such coating. The liposomes contain, in liposome-entrapped form, a chemotherapeutic agent. Covalently attached to the distal ends of a portion of chains in the liposome polyethylene glycol surface coating, are antibodies or antibody fragments effective to bind to an antigen specific to the affected B-cells or T-cells.

The liposomal surface coating is provided by a coating of polyethylene glycol having a molecular weight of between about 500–10,000 daltons. Preferably, the molecular weight is between 500–5,000 daltons, most preferably between 500–2,000 daltons.

In a preferred embodiment, the antibodies attached to the distal PEG ends of the liposomes are anti-CD19, anti-CD20 or anti-CD22, for specific binding to a B-cell antigen. Such a composition is effective for treatment of disorders derived from B-cells, such as multiple myeloma, acute lymphocytic leukemia and B-cell lymphoma.

In another embodiment, the attached antibodies are anti-CD4 or anti-CD8 for binding to a T-cell antigen, for treatment of disorders such as T-cell lymphoma or acute lymphocytic leukemia.

The liposomes may contain, in liposome entrapped form, a therapeutic agent, such as doxorubicin or vincristine.

These and other objects and features of the invention will be more fully appreciated when the following detailed description of the invention is read in conjunction with the accompanying drawings.

BRIEF DESCRIPTION OF THE DRAWINGS

FIGS. 2A–2B show steps of one synthetic approach for forming a maleimide of a DSPE carbamide of polyethylene glycol his (amine) which can be used for further coupling to an antibody or antibody fragment;

(FIG. 7A) and at 4° C. (FIG. 7B), and in H9 cells at 37° C. (FIG. 7C), where binding is expressed in nmoles phospholipid/$10^6$ cells, as a function of phospholipid concentration, in nmoles/ml, of immunoliposomes having an attached anti-CD19 antibody (■), liposomes (□) and immunoliposomes plus excess free anti-CD19 antibody (▽);

FIGS. 10A–10G show FACS analyses for the association of fluorescent-labelled liposomes with Namalwa cells, plotting the relative number of cells as a function of the fluorescence intensity for the cells alone (A), free anti-CD19 antibody (B), immunoliposomes with attached anti-CD19 antibody (C), conventional liposomes (no PEG coating) (D), liposomes (E), immunoliposomes with an attached isotype matched, non-specific $IgG_{2A}$ antibody (F), and excess free anti-CD19 antibody plus immunoliposomes with attached anti-CD19 antibody (G);

FIGS. 11A–11F show FACS analyses for the association of fluorescent-labelled liposomes with human spleen cells, plotting the relative number of cells as a function of the fluorescence intensity for the cells alone (A), free anti-CD19 antibody (B), immunoliposomes with attached anti-CD19 antibody (C), conventional liposomes (no PEG coating) (D), liposomes (E), and immunoliposomes with an attached non-specific $IgG_{2A}$ antibody (F);

FIGS. 12A–12H show FACS analyses for the association of fluorescent-labelled liposomes with CD19-negative T cells, plotting the relative number of cells as a function of the fluorescence intensity for the T cells alone (A), free anti-CD4-PhE antibody (B), anti-CD8-PhE antibody (C), free anti-CD19-FITC antibody (D), conventional liposomes (E), liposomes (F), immunoliposomes with attached anti-CD19 antibody (G) and immunoliposomes with an attached non-specific $IgG_{2A}$ antibody (H);

DETAILED DESCRIPTION OF THE INVENTION

The present invention provides a method of treating a subject having a disorder characterized by a neoplasm of B-lymphocyte or T-lymphocyte lineage cells. Such disorders include, but are not limited to, blood plasma disorders which are derived from a B-cell origin and include multiple myeloma, Waldenstrom's macroglobulinemia, and primary amyloidosis. Lymphomas, both B-cell lymphoma and T-cell lymphoma, and acute lymphocytic leukemia are also disorders suitable for treatment in accordance with the method of the invention.

The method includes administering to the subject a suspension of liposomes having an extended blood circulation time by virtue of a surface coating of polyethylene glycol chains, and containing a liposome-entrapped drug. Antibodies or antibody fragments are attached covalently to the liposomes, as described below, for specific targeting of the immunoliposomes to the affected cells.

I. Definitions

The following terms, as used herein, have the meanings as indicated:

Immunoliposome refers to a liposome having a surface coating of polyethylene glycol (PEG) chains, and antibodies or antibody fragments covalently attached to the distal or free ends of a portion of the PEG chains. The immunoliposome may alternatively contain a surface coating of PEG chains, a portion of which have a ligand covalently attached, at the free ends, that recognizes a specific target molecule or epitope. The immunoliposome may have an entrapped therapeutic agent.

Liposome refers to a liposome having a surface coating of PEG chains, with no surface-attached antibody. The liposome may have an entrapped therapeutic agent.

II. Immunoliposome Compositions

Figure 1:
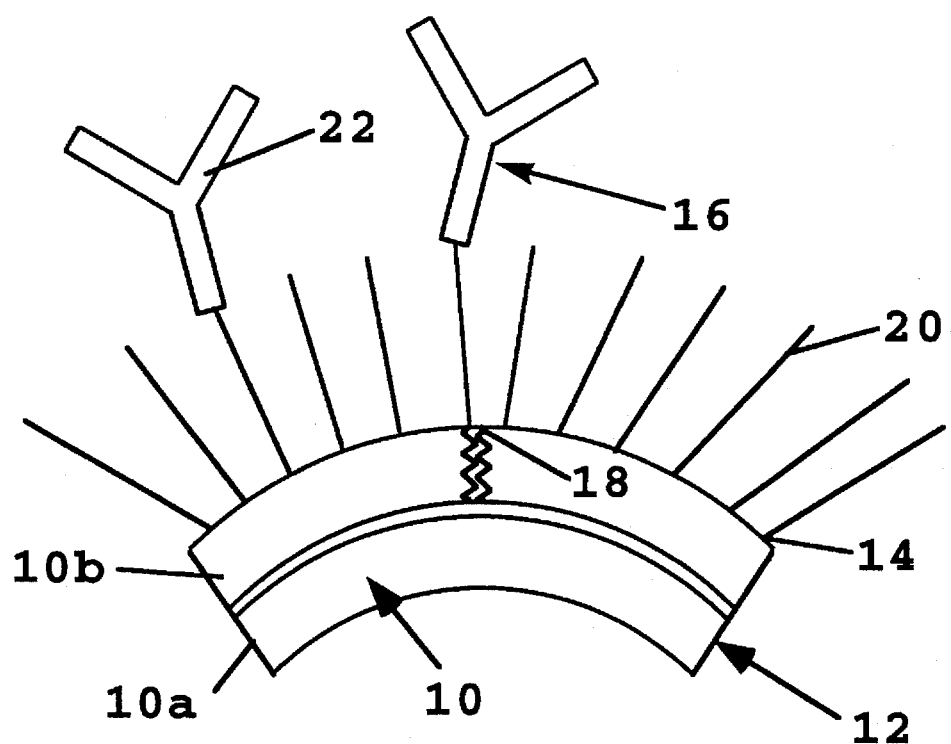
FIG. 1 illustrates the antibody-liposome composition of the present invention, in which antibodies or antibody fragments are attached to the free ends of polyethylene glycol chains surrounding a liposome.

An immunoliposome prepared in accordance with the invention is illustrated in FIG. 1. The figure shows a portion of the outer bilayer 10 of a liposome 12 having an outer surface 14. The liposome may include additional bilayers. The outer bilayer itself is composed of confronting lipid layers 10a and 10b which are the interior and exterior lipid layers, respectively, of the bilayer, each layer being composed of vesicle-forming lipids, such as phospholipids and cholesterol. Methods for forming liposomes suitable for use in the composition are described below.

The liposome includes an antibody or an antibody fragment, such as antibody 16, which is bound to the outer liposome surface by covalent attachment to hydrophilic polymer chains, such as chains 20, which are also carried on the liposome's outer surface. The polymer chains form a polymer layer about the liposome surface which allows the liposomes to circulate in the bloodstream over an extended period of time compared to liposomes lacking the polymer coating.

The antigen recognition region, such as antigen recognition region 22, of the antibody molecule is accessible for binding to antigens at a target site. The polymer coating on the liposome surface does not affect antigen-antibody interactions. Antibody molecules suitable for use in the invention, and methods of their attachment to the liposome are described below.

The polymer chains are preferably polyethylene glycol (PEG) chains having molecular weights between about 500 and 10,000 daltons, corresponding to polymer chain lengths of about 22 to 220 ethylene oxide units. Preferably the PEG molecular weight is between 500–5,000 daltons, most preferably between 500–2,000 daltons.

The polymer chains are covalently attached to the polar head groups of vesicle-forming lipids as described in co-owned U.S. Pat. No. 5,013,556, herein incorporated by reference.

The polymer chain is attached to the liposome through the polar head group of a lipid, such as lipid 18, in the outer layer 10 of the liposome bilayer. The chain contains a reactive functionalized group at its free end for coupling to the antibody, to be described.

A liposome having an antibody attached to the liposome outer surface by a polymer chain, as illustrated in FIG. 1, is referred to herein as an immunoliposome. The antibody is positioned at the distal, or free ends of a portion of the polymer chains. As used herein, liposome refers to a liposome having a surface coating of PEG, but lacking an attached antibody.

A. Lipid Components

The liposomes of the present invention are generally composed of at least three types of lipid components. A first type, which will form the bulk of the liposome structure, includes any amphipathic lipid having hydrophobic and polar head group moieties, and which (a) can form spontaneously into bilayer vesicles in water, as exemplified by the phospholipids, or (b) is stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids of this type are preferably ones having two hydrocarbon chains, typically acyl chains, and a polar head group. Included in this class are the phospholipids, such as phosphatidylcholine (PC), phosphatidylethanolamine (PE), phosphatidic acid (PA), phosphatidylglycerol (PG), phosphatidylinositol (PI), and sphingomyelin (SM), where the two hydrocarbon chains are typically between about 14–22 carbon atoms in length, and have varying degrees of unsaturation. The above-described lipids and phospholipids whose acyl chains have a variety of degrees of saturation can be obtained commercially, or prepared according to published methods. Other lipids that can be included in the invention are glycolipids.

A second lipid component includes a vesicle-forming lipid which is derivatized with a polymer chain. The vesicle-forming lipids which can be used are any of those described above for the first vesicle-forming lipid component. Vesicle-forming lipids with diacyl chains, such as phospholipids, are preferred. One exemplary phospholipid is phosphatidylethanolamine (PE) with a reactive amino group which is convenient for coupling to an activated polymer. An exemplary PE is distearyl PE (DSPE).

The preferred polymer in the derivatized lipid is polyethyleneglycol (PEG), preferably as a PEG chain having a molecular weight between 500–10,000 daltons, more preferably between 500–5,000 daltons, most preferably between 500–2,000 daltons. Once a liposome is formed, the polyethylene glycol chains provide a surface coating of hydrophilic chains sufficient to extend the blood circulation time of the liposomes in the absence of such a coating.

Other hydrophilic polymers which may be suitable for use in forming the second lipid component of the invention include polyvinylpyrrolidone, polymethyloxazoline, polyethyloxazoline, polyhydroxypropyl methacrylamide, polymethacrylamide, polydimethylacrylamide, polylactic acid, polyglycolic acid, and derivatized celluloses, such as hydroxymethylcellulose or hydroxyethylcellulose.

A third type of lipid component for use in the invention is a vesicle-forming lipid which has been modified for coupling antibody molecules to the liposome. In one embodiment, the modified lipid contains a hydrophilic polymer chain attached to the lipid. The hydrophilic polymer is typically end-functionalized for coupling antibodies to its functionalized end. The functionalized end group is preferably a hydrazide or hydrazine group which is reactive toward aldehyde groups, although any of a number of PEG-terminal reactive groups for coupling to antibodies may be used. Hydrazides can also be acylated by active esters or carbodiimide-activated carboxyl groups. Acyl azide groups reactive as acylating species can be easily obtained from hydrazides and permit attachment of amino-containing molecules. In another embodiment, the functionalized end group is (2-pyridyldithio) propionamide), for coupling the antibody to the liposome through a disulfide linkage.

A preferred polymer in the derivatized lipid is polyethylene glycol (PEG). Other hydrophilic polymers which may be suitable for lipid derivatization include end-functionalized polyvinylpyrrolidone, polymethyloxazoline, polyethyloxazoline, polyhydroxypropyl methacrylamide, polymethacrylamide, polydimethylacrylamide, polylactic acid, polyglycolic acid, and derivatized celluloses, such as hydroxymethylcellulose or hydroxyethylcellulose.

Additionally, the liposomes may include lipids that can stabilize a vesicle or liposome composed predominantly of phospholipids. The most frequently employed lipid from this group is cholesterol at between 25 to 40 mole percent. At between 0 to 20 mole percent cholesterol in a bilayer, separate domains exist containing cholesterol and phospholipids and pure phospholipid (Mabrey). These bilayers show an increased permeability to water (Tsong). At mole percentages above 50% cholesterol starts destabilizing the bilayer.

B. Liposome-entrapped Compound

A variety of therapeutically active compounds are suitable for delivery by the liposome composition. The compound is useful, in one embodiment, for treatment of a plasma cell disorder, such as multiple myeloma, which is characterized by neoplasms of B-lymphocyte lineage cells. In another embodiment, the therapeutic agent is effective against disorders derived from T-cell origins, such as T-cell lymphoma.

Therapeutic agents preferred for treatment of multiple myeloma include melphalan, cyclophosphamide, prednisone, chlorambucil, carmustine, dexamethasone, doxorubicin, vincristine, lomustine, and interferon.

Typical doses for standard chemotherapy treatment for some of these drugs are as follows: melphalan, 8 mg/m$^2$ body surface area per day; cyclophosphamide, 200 mg/m$^2$ per day; chlorambucil, 8 mg/m$^2$ per day; prednisone 25–60 mg/m$^2$ per day, vincristine (1.4 mg/m$^2$) and doxorubicin (60–75 mg/m$^2$).

In the present invention, the therapeutic agent is entrapped in an immunoliposome, by methods discussed below, for administration parenterally to a subject. The dose used for liposome administration may initially be based on the standard chemotherapeutic dose and adjusted accordingly over the course of treatment by monitoring the disease progression.

The liposome-entrapped compound may also be an imaging agent for tracking progression of a disease. Imaging agents include chelates of radionuclides, such as technetium-99, indium-111, and iodine-124.

C. Antibody Molecules

Antibodies as used herein are monoclonal antibodies or antibody fragments which are used for targeting antigens specific to the B-cells or the T-cells in the affected individual. These antibodies or antibody fragments are typically derived from hybridomas that show positive reactivity toward the affected B-cells and T-cells, as will be shown.

More generally, a ligand with specific recognition to a B-cell or T-cell epitope can be attached to the distal ends of the liposome-attached PEG chains. For example, a specific ligand, e.g., a carbohydrate or lectin, that will bind to a B-cell epitope, including, CD19, CD20, CD22, or CD77, may be attached to the liposome, to be described in more detail below.

In experiments performed in support of the present invention, anti-CD19 antibodies were used to target a liposome-entrapped drug, doxorubicin, to malignant B-cells obtained from, for example, the blood from persons afflicted with multiple myeloma. The antibody recognizes a unique epitope, the CD19 surface antigen, on the cells. The immunoliposomes are specific to the B-cells, avoiding toxicity to the T cell population, thus preserving T cell-mediated immunity.

III. Preparation of Immunoliposomes

This section describes the synthesis of some exemplary modified lipids for use in coupling antibodies or antibody fragments to a liposome surface. Also described are methods of preparing liposomes which incorporate the modified lipids, and for coupling antibodies to a liposome surface via the modified lipids.

A. Modified Lipid Preparation

PEG-functionalized lipids may be activated to contain any of a number of terminal reactive groups suitable for coupling to antibodies or antibody fragments by standard coupling methods known in the art. Generally, the PEG chains are functionalized to contain reactive groups suitable for coupling with, for example, sulfhydryls, amino groups, and aldehydes or ketones (typically derived from mild oxidation of carbohydrate portions of an antibody) present in an antibody. Examples of such PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive).

For compositions utilizing liposomes having a surface coating of PEG chains, one advantage of activating the PEG terminal group of the functionalized lipid prior to liposome formation is that a broad range of reaction solvents and reaction conditions may be employed. Further, the liposomes themselves are not exposed to the activating reagents used to introduce the terminal PEG reactive functionality. Thus, the need to remove reagent contaminants from the liposomes is avoided.

It will also be appreciated that in some instances, the activation reactions may optionally be performed after incorporation of polymer-functionalized lipid into liposomal carriers. In some coupling reactions it may be more desirable to activate the terminal PEG groups on preformed liposomes. One advantage of this approach is that the activation reaction is confined to the outer, surface-accessible lipids, and thus the activated groups can be completely quenched prior to use of the composition in therapy. The approach is also preferred for reactions in which the activated PEG termini are unstable in water.

1. Preparation of DSPE derivatized with a PEG chain containing an activated maleimide group at the chain's free end.

Maleimides are widely used protein modifying reagents and are especially useful when the maleimide is one of two functional groups in a heterobifunctional crosslinking reagent. The reaction of maleimides with sulfhydryl groups involves Michael addition of the mercaptan group to the activated double bond. Reaction with amino groups occurs by the same mechanism, but at a much slower rate. Since mercaptan is the most reactive species, particularly at neutral pH, the maleimide group can be used to target sulfhydryl groups and good selectivity is usually achieved.

Figure 2B:
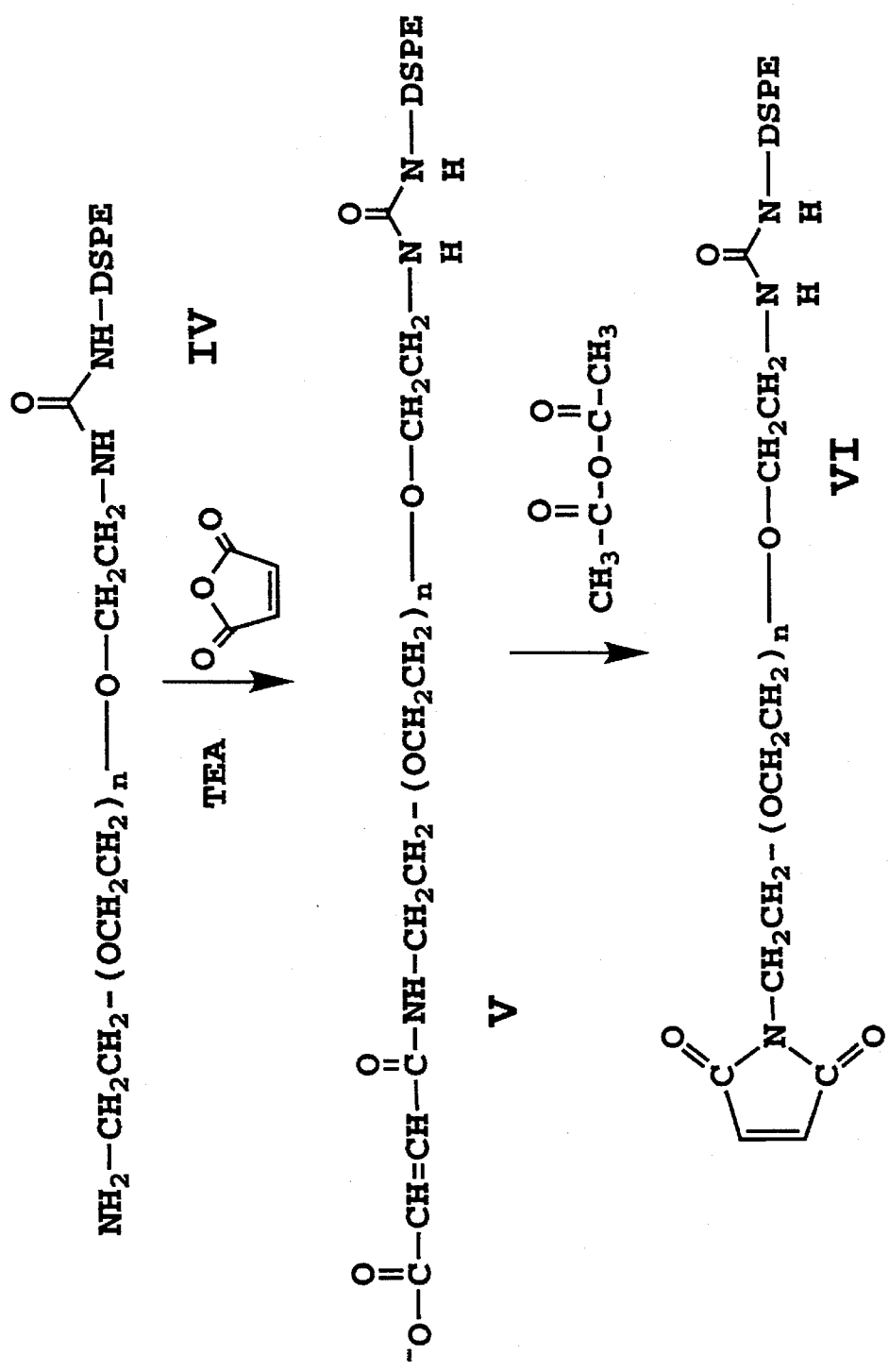

In one embodiment of the present invention, a derivatized lipid such as PE- or DSPE-PEG is prepared to contain a terminal maleimide group, as illustrated in FIG. 2B. The lipid, either after or prior to incorporation into liposomes, is then reacted with a sulfhydryl-containing antibody under suitable coupling conditions.

In one exemplary approach, such as that illustrated in FIGS. 2A–2B, and described in detail in Example 1, DSPE or any similar lipid is derivatized with a PEG chain having an activated maleimide group at the chain's free end. Initially, PEG bis (amine) (compound I) is reacted with 2-nitrobenzene sulfonyl chloride to generate the monoprotected product (compound II). Compound II is reacted with carbonyl diimidazole in triethylamine (TEA) to form the imidazole carbamide (e.g., urea) of the mono 2-nitrobenzenesulfonamide (compound III).

Compound III is reacted with DSPE in TEA to form the derivatized DSPE lipid protected at one end with 2-nitrobenzyl sulfonyl chloride. The protecting group is removed by treatment with acid to give the DSPE-PEG product (compound IV) having a terminal amine on the PEG chain. Reaction with maleic anhydride gives the corresponding end-functionalized product (compound V), which on reaction with acetic anhydride gives the desired DSPE-PEG-maleimide product (compound VI). Compound VI is reactive with sulfhydryl groups, for coupling antibodies through a thioether linkage.

2. Preparation of DSPE-PEG-Hz (where Hz=hydrazide)

A. The reaction scheme shown in FIG. 3A illustrates the preparation of a derivatized lipid (DSPE) in which the free PEG end is functionalized to contain a hydrazide.

Methods for preparing heterobifunctional PEG derivatives, such as starting compound XIX, have been described by Zalipsky, et al (1986; 1990). Such PEG derivatives are useful in coupling to lipids, such as PE or DSPE, at one functionalized PEG terminus, and to antibodies at the other functionalized polymer end.

Figure 3A:
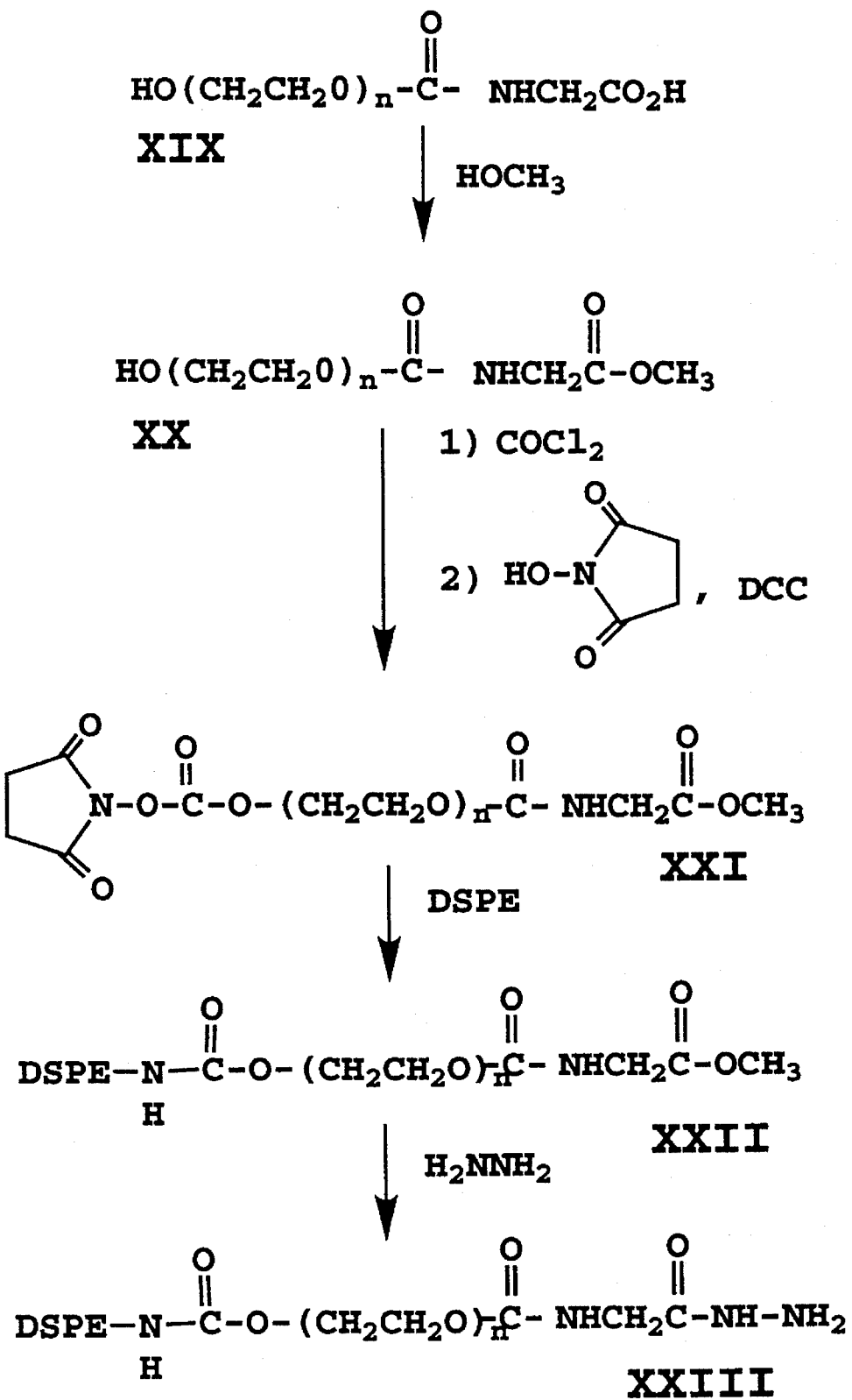
FIG. 3A shows an exemplary method for synthesizing a DSPE lipid derivatized with a PEG chain containing a terminal hydrazide group for coupling to aldehyde or ketone groups of an antibody.

In the reaction illustrated in FIG. 3A, an α-hydroxy-ω-carboxylic acid PEG derivative (compound XIX) (Zalipsky, et al., 1990) is esterified with methanol to protect the terminal acid group by formation of the corresponding ester (compound XX). The terminal hydroxyl group is then converted into a functional group reactive towards primary amines (Zalipsky, et al., 1992a), for example, a succinimidyl carbonate (SC) derivative (compound XXI). This compound is formed, for example, by reacting compound XX with phosgene followed by subsequent reaction with N-hydroxysuccinimide (Zalipsky, et al., 1992b). The resulting activated PEG compound, SC-PEG-C(O)NHCH$_2$CO$_2$—Me (compound XXI) reacts with a lipid amine such as PE or DSPE at the reactive succinimidyl carbonate group to form the functionalized lipid, DSPE-PEG-C(O)NHCH$_2$CO$_2$—Me (compound XXII). The methyl ester can be readily hydrazinolyzed to yield DSPE-NHCO$_2$-PEG-C(O)NHCH$_2$C(O)—N$_2$H$_3$ (compound XXIII), as shown.

This hydrazide-containing PEG-lipid is incorporated into liposomes by conventional methods. The hydrazide group can be used for attachment of antibodies through their oxidized carbohydrate moieties. Typically, a mild oxidant such as sodium periodate is used to oxidize glycoproteins by converting vicinal hydroxyl groups to reactive aldehydes, which then can react with hydrazide groups on the PEG chains. The antibody-PEG linkages thus formed, hydrazones, are generally stable at pH$\geq$7.5, but are cleavable by acid catalyzed hydrolysis at lower pH values.

B. In an alternate synthetic approach, illustrated in FIG. 3B and described in Example 2, PEG-functionalized DSPE containing a terminal PEG-hydrazide is prepared.

First PEG is reacted with ethyl isocyanatoacetate in the presence of triethylamine to generate mono and di-end carboxylated species of PEG, where the carboxylic acid functions are connected to the PEG skeleton via intervening carbamate bonds. The monocarboxylated species is purified by ion-exchange chromatography on DEAE-Sephadex (compound XXIX, identical to compound XIX). Compound XXIX is reacted with tert-butyl carbazate to generate the ω-hydroxy-α-Boc-hydrazide derivative of PEG (compound XXX). The hydroxyl terminus of PEG is then activated by reaction with disuccinimidyl carbonate to form compound XXXI prior to reaction with DSPE to generate the desired lipid-PEG-α-Boc hydrazide product (compound XXXII). Compound XXXII is deprotected with 4M HCl in dioxane to form the free hydrazide group. Lipid-PEG-hydrazide may then be incorporated into liposomes. The hydrazide groups are reactive towards aldehydes, which as described above, can be generated on numerous biologically relevant compounds.

3. Preparation of DSPE-PEG-PDP (PDP=(2-pyridyldithio) propionamide)

Figure 4:
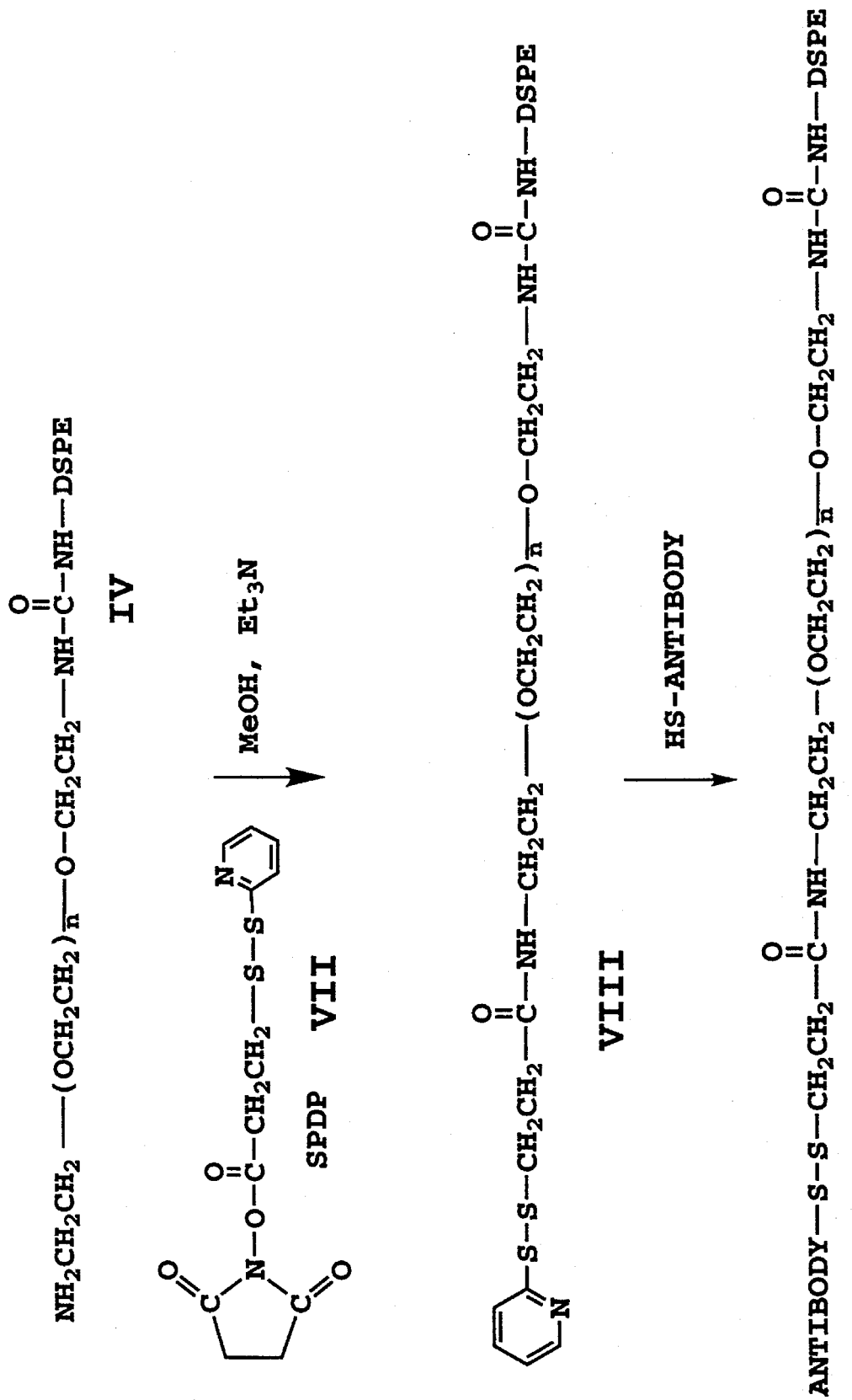
FIG. 4 shows steps for the synthesis of a disulfide linkage-containing propionamide of a DSPE carbamide of polyethylene glycol bis (amine) and subsequent covalent coupling to a thiol group of an antibody.

FIG. 4 illustrates an exemplary synthesis of another derivatized lipid useful for coupling to sulfhydryl-containing antibodies. Here the DSPE-PEG lipid (compound IV) described above is treated with N-succinimidyl-3-(2-pyridyldithio) propionamide, SPDP, (compound VII) to form DSPE-PEG-PDP lipid (compound VIII). The reaction is described in detail in Example 3.

The compound can, for example, react with a sulfhydryl group of an antibody to couple the antibody through a disulfide linkage, as illustrated in FIG. 4 (compound XXXIV).

4. Preparation of PEG-functionalized lipids containing a terminal PEG group for reacting with amines.

As discussed above, lipids functionalized to contain PEG chains with a terminal amino-reactive group may also be utilized to couple antibodies in accordance with the present invention.

In one such approach, a heterobifunctional PEG compound such as an α-hydroxy-ω-carboxy derivative of PEG can be coupled to a lipid containing a terminal amino group, e.g., DSPE, by reaction with N-hydroxysuccinimide in the presence of a coupling agent such as dicyclohexylcarbodiimide, DCC. The resulting intermediate, the N-hydroxysuccinimide (NHS) ester of α-hydroxy-PEG, is then suitable for coupling to an amino-end containing lipid such as DSPE by displacement of the NHS group to form a α-hydroxy-PEG-DSPE conjugate, linked by an amide bond. The α-hydroxy group of PEG can then be further activated, such as by reaction with disuccinimidyl carbonate (DSC), to form an α-succinimidyl carbonate-PEG-DSPE compound suitable for coupling to a variety of compounds containing reactive amino groups.

B. Liposome Preparation

The liposomes may be prepared by a variety of techniques, such as those detailed in Szoka et al, 1980. Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns. In an alternative method, liposomes are prepared by vortexing the dried lipid film in a buffered aqueous solution (Olson).

Liposome compositions are typically prepared with lipid components present in a molar ratio of about 30–75 percent vesicle-forming lipids, 25–40 percent cholesterol, and 1–20 percent polymer-derivatized lipid employed for antibody coupling. One exemplary liposome formulation includes hydrogenated soy phosphatidylcholine (HSPC) and cholesterol (chol), in a 2:1 molar ratio. Between 1–5 mole % of DSPE-PEG-hydrazide is added to form liposomes with a surface coating of PEG, with end-functionalized chain ends for attaching an antibody or antibody fragments. Another exemplary liposome formulation includes HSPC:chol in a 2:1 molar ratio, along with 4 mol % DSPE-PEG and 1 mol % DSPE-PEG-PDP.

Generally, a therapeutic drug is incorporated into liposomes by adding the drug to the vesicle-forming lipids prior to liposome formation, as described below, to entrap the drug in the formed liposome. If the drug is hydrophobic, it can be added directly to the hydrophobic mixture, whereas a hydrophilic drug can be added to the aqueous medium which covers the thin film of evaporated lipids.

Alternatively, the drug may be incorporated into preformed liposomes by active transport mechanisms, such as remote loading. Typically, in this case drug is taken up in liposomes in response to a gradient, such as an ammonium sulphate gradient, as described, for example, in U.S. Pat. No. 5,192,549, or a potassium or hydrogen ion concentration differential (Mayer, 1986; Mayer, 1989).

One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin 1990).

C. Antibody Coupling to Liposome Surface

Antibodies may be attached to a liposome surface by covalent coupling to a modified lipid, such as DSPE-PEG-hydrazide, DSPE-PEG-PDP, or like modified lipids such as those described above. The mode of antibody binding to an end-functionalized PEG chain on a derivatized lipid will depend upon the desired mode of antibody binding (e.g., via reactive amino groups, aldehyde groups, sulfhydryls, exposed carboxyls). In attaching an antibody to a PEG-functionalized lipid, the antibody preferably does not suffer any loss of activity.

The modified lipid containing the end-functionalized polyethylene glycol chain is incorporated into liposomes and, after liposome formation, the end-functionalized group can react with an antibody for antibody coupling to a liposome surface.

Alternatively, an antibody-lipid derivative may be first formed and then incorporated into a liposome. For example, an antibody may be coupled to a terminal maleimide group of a DSPE-PEG molecule, as described above and in copending, co-owned PCT application 94/03457. The antibody-coupled DSPE-PEG molecule is then employed to form vesicles.

In a preferred embodiment, the polymer contains a terminal hydrazide group for coupling to an antibody via the oxidized carbohydrate moieties of the antibody, as detailed in FIG. 5 and Example 4 below. Briefly, vicinal hydroxyl groups in the antibody molecule are oxidized to aldehydes by mild periodate oxidation. The oxidized protein is then added to liposomes containing a hydrazide-functionalized PEG-lipid, such as DSPE-PEG hydrazide, and incubated overnight. Unbound antibodies are then separated from the antibody-liposomes by gel filtration.

In an alternative coupling method such as that shown in FIG. 4, sulfhydryl groups present in an antibody molecule are attached to an end-functionalized PEG-lipid by formation of a disulfide linkage.

IV. Method of Treatment

According to an important aspect of the invention, it has been found that antibodies can be attached to the PEG chain free ends without a significant loss of blood circulation time of the liposomes, allowing the immunoliposomes to remain in circulation in order to localize at the target B-cells or T-cells through antibody-antigen specific interactions. As a result, a significant therapeutic enhancement in treatment over long-circulating liposomes in the absence of surface attached antibodies is possible.

The studies in Part A below illustrate how the immunoliposome composition is able to increase the therapeutic effect of a compound entrapped in the immunoliposomes, when measured against the same long-circulating liposomes, but in the absence of surface-attached antibodies. In vitro binding studies and internalization studies are reported in Part B. Part C illustrates with in vivo studies the improved therapeutic effect achievable by the treatment method of the invention.

A. Therapeutic Efficacy of Immunoliposome Composition in vivo

Experiments were performed to investigate the half-life in the bloodstream and the tissue biodistribution of the immunoliposome composition. For these experiments liposomes containing PEG end-functionalized with a hydrazide group covalently linked to sheep IgG were prepared as described in Example 5.

The tissue biodistribution of liposomes containing $^{125}$I-tyraminylinulin with and without covalently attached IgG antibodies is shown in Table 1 (Example 5A). It can be seen that the tissue biodistribution of liposomes containing antibody covalently attached to the end of a PEG chain by a hydrazide group is very similar to those of liposomes containing nonfunctionalized PEG chains. Liposome biodistribution was determined for the blood, liver, spleen, lung, heart and carcass.

Figure 6:
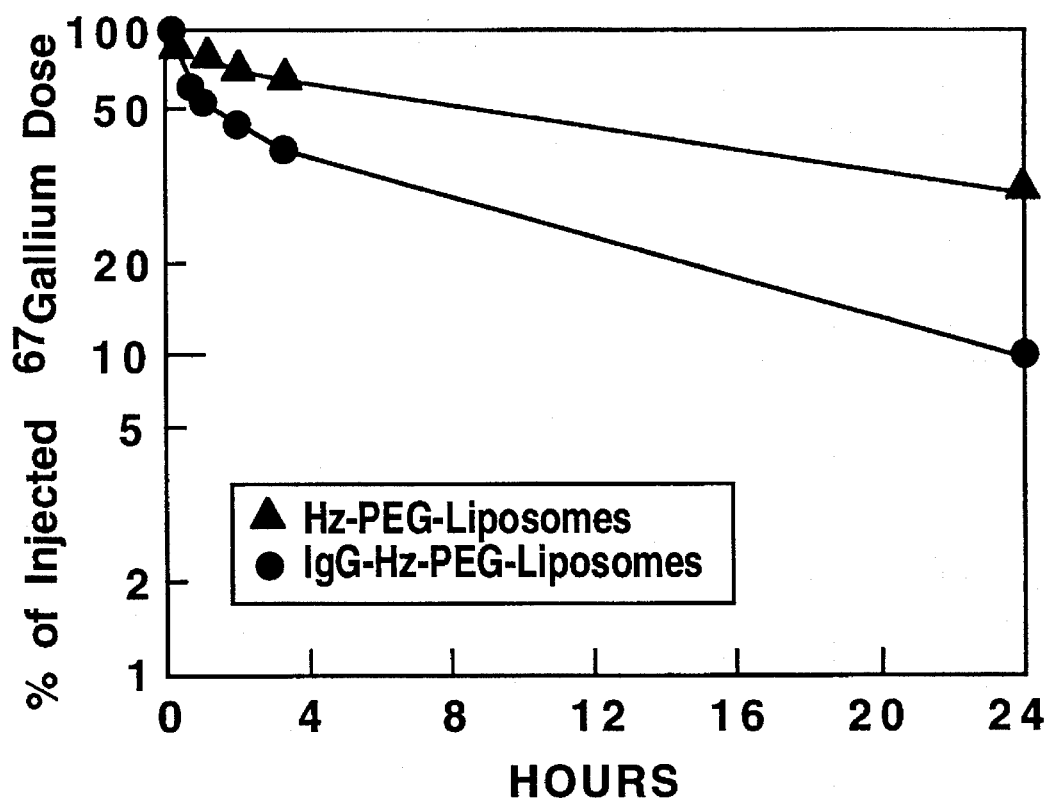
FIG. 6 is a plot of drug residence time in the blood, expressed in terms of percent injected dose as a function of hours after intravenous injection in rats, for liposomes containing $^{67}$Gallium and a bound antibody IpG (●) or liposomes with no bound antibody (▲)

Liposomes like those above except containing entrapped $^{67}$Gallium were prepared and administered to rats to measure the blood circulation time, as described in Example 5B. The levels of liposome-entrapped $^{67}$Gallium were measured at regular intervals following administration of the two liposome formulations and the results are shown in FIG. 6. As seen, both liposome formulations gave good blood circulation lifetime, with more than 10% of the injected marker being retained in the bloodstream after 24 hours. By contrast, it is known from similar studies (Martin 1993) that liposomes not containing PEG have only about 5% marker retention in the blood 3 hours or less after iv administration and no measurable liposome label at 24 hours.

B. In vitro Binding Studies and Cell Cytotoxicity

In vitro experiments were done to determine the binding of liposomes, with or without attached antibodies, to several different cell lines. Binding experiments were done with the CD19+ human B-cell lymphoma cell line (Namalwa), T-cell lymphoma cell line (H9 cells), human spleen cells or peripheral blood mononuclear cells obtained from multiple myeloma patients.

Binding experiments were conducted as described in Example 6, using radiolabeled liposomes and fluorescently labeled liposomes, analyzed by fluorescent activated cell sorting (FACS) and by two color flow cytometry.

Liposomes were prepared as described in Example 6A, and antibody coupling was done using DSPE-PEG-Hz. Radiolabeled liposomes contained $^3$H-cholesterol hexacyldecyl ether ($^3$H-CHE) and fluorescently labelled liposomes contained the dye nitrobenzoxadiazol-amino-PE (NBD-PE).

Figure 7A:
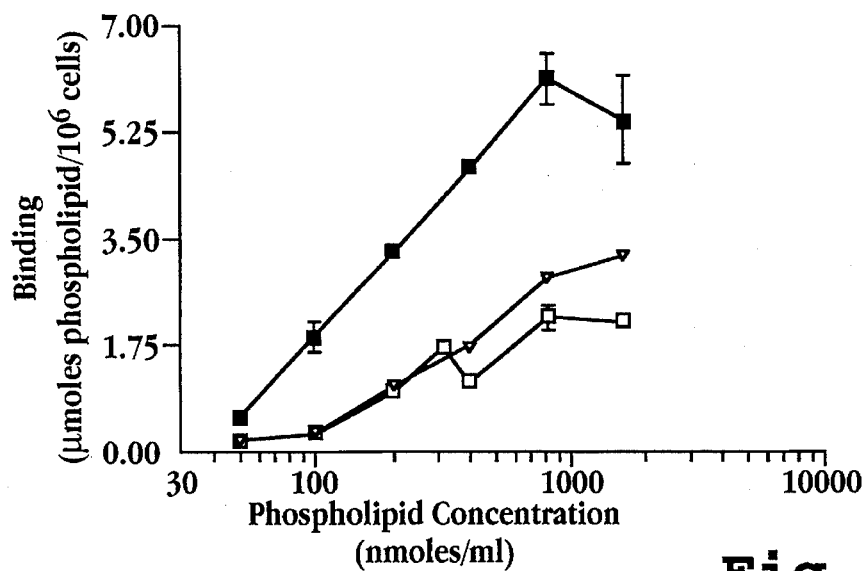
FIGS. 7A–7C are plots showing binding in Namalwa cells at 37° C.
Figure 7B:
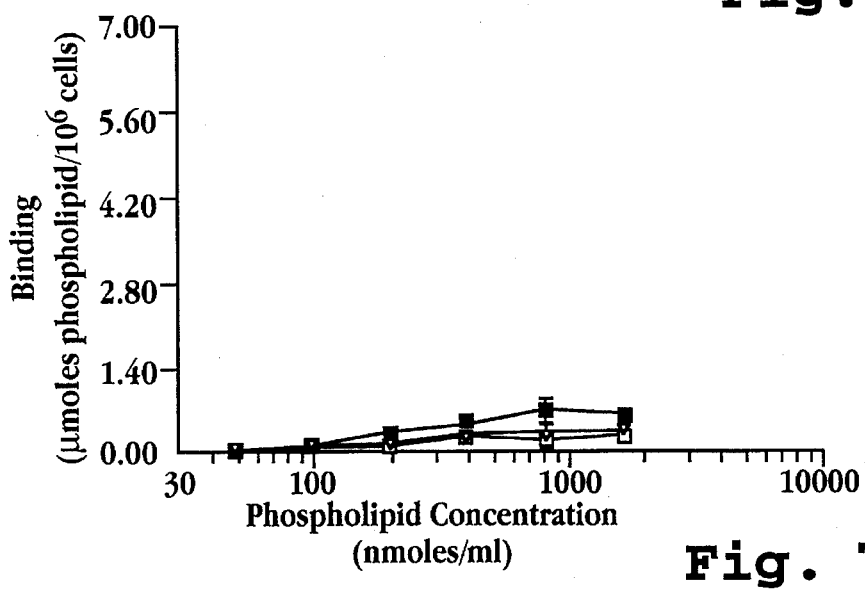

FIGS. 7A–7B show the binding of immunoliposomes having an attached anti-CD19 antibody (■), of liposomes (□), and of immunoliposomes plus excess free anti-CD19 antibody (▽) to CD19+ Namalwa cells at 37° C. (FIG. 7A) and at 4° C. (FIG. 7B). The CD19+ human B-lymphoma cell line has a 3-fold higher specific binding of immunoliposomes having an attached anti-CD19 antibody in comparison to liposomes lacking the attached antibody. This binding could be competitively blocked by addition of excess free anti-CD19 antibody, as indicated by the (▽) symbols. In general, binding studies are not highly temperature dependent, and the significant decrease in binding at 4° C. may be an indication that the liposomes are internalized by the cells, as will be discussed below.

Figure 7C:
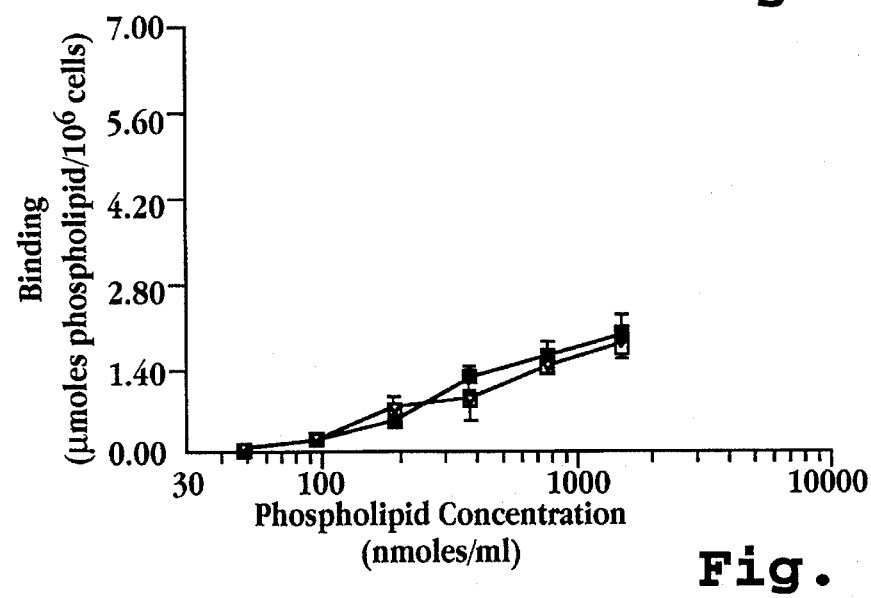

FIG. 7C shows binding by CD19-negative T-cells, using the same formulations indicated above in FIG. 7A. Binding of the immunoliposomes (■) to the CD19- T-cell line is significantly lower than to the B-cell line, and little specific binding to the T-cells is observed, as the T-cells do not have a specific epitope for the anti-CD19 antibody.

Figure 8:
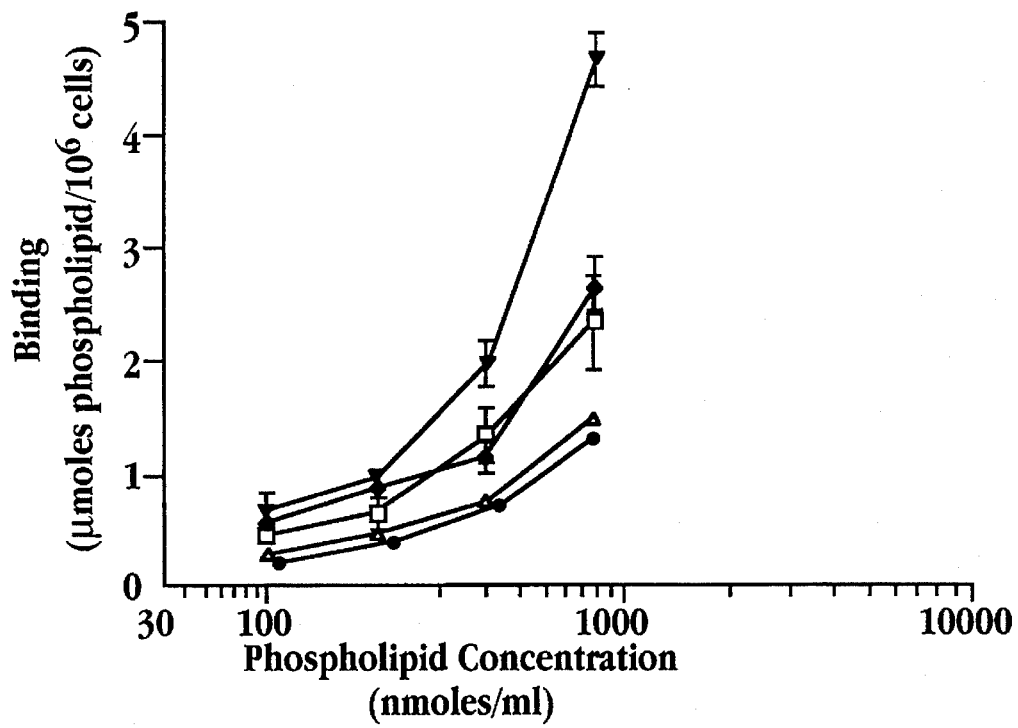
FIG. 8 shows binding in human spleen cells of immunoliposomes having an attached antibody via a hydrazide linkage (☆), immunoliposomes having an attached antibody via a PDP linkage (♦), liposomes with an active hydrazide terminus (□), liposomes with an active PDP terminus (△) and for conventional liposomes (no PEG coating) (●)
Figure 9:
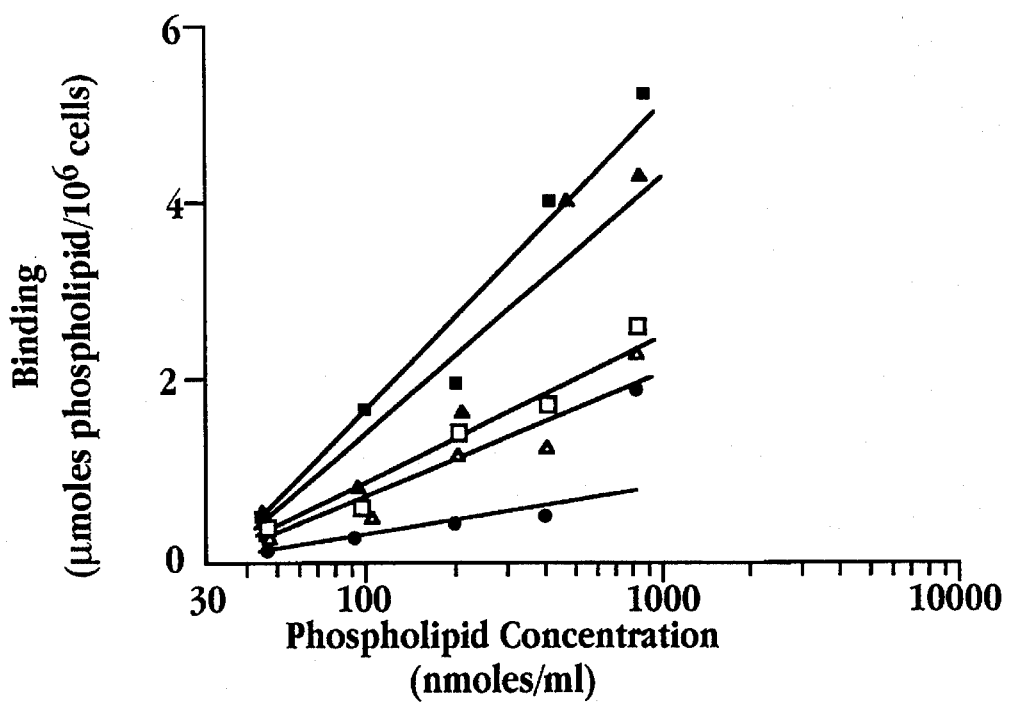
FIG. 9 shows binding in human peripheral blood mononuclear cells of immunoliposomes having an attached antibody via a hydrazide linkage (■), immunoliposomes having an attached antibody via a PDP linkage (▲), liposomes with an active hydrazide terminus (□), liposomes with an active PDP terminus (△) and for conventional liposomes (no PEG coating) (●)
Figure 13A:
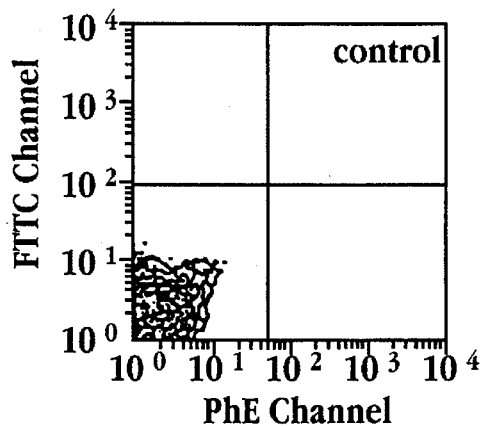
FIGS. 13A–13F show two color flow cytometry for selective recognition of immunoliposomes by B cells using FACScan, showing the cells alone (A), anti-CD19-FITC and anti-CD4,8-PhE to stain the B and T cells, respectively (B), NBD-immunoliposomes with anti-CD19 attached and anti-CD4,8-PhE (C), NBD-immunoliposomes with anti-CD19 attached and anti-CD20-PhE (D), NBD-liposomes and anti-CD4,8-PhE (E) and NBD-liposomes and anti-CD20-PhE (F)
Figure 13B:
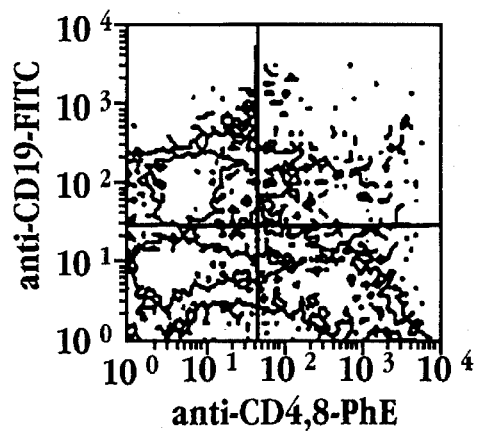
Figure 13C:
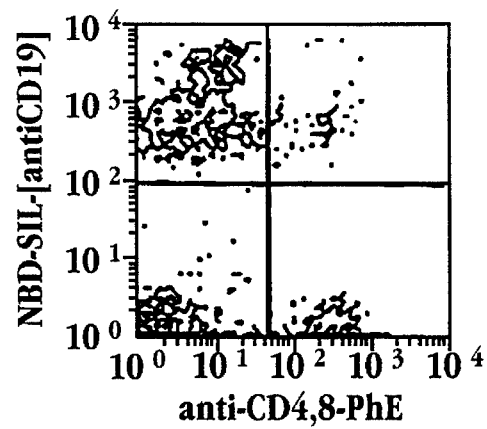
Figure 13D:
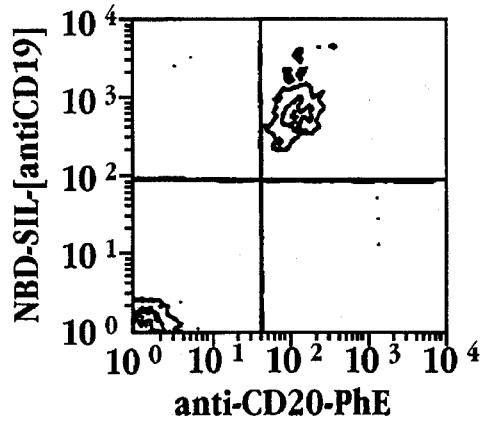
Figure 13E:
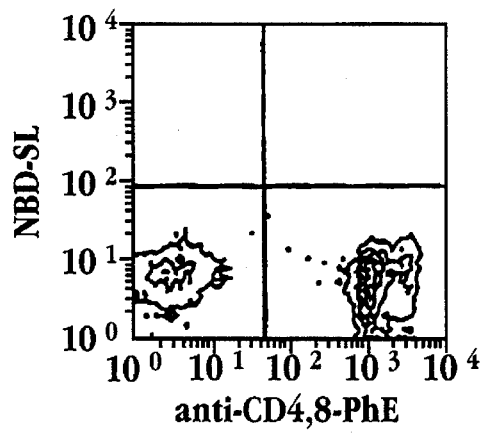
Figure 13F:
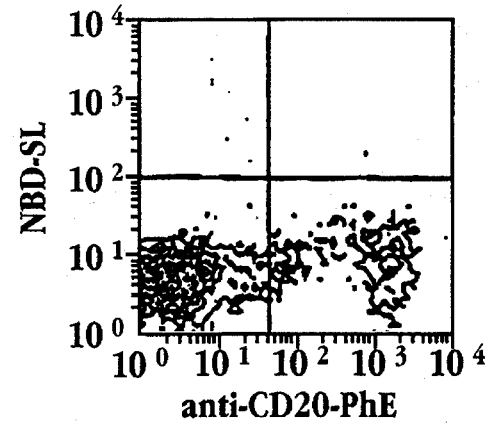

FIGS. 8 and 9 are plots similar to FIG. 7, showing binding to human spleen cells (FIG. 8) and to human peripheral blood mononuclear cells (PBMC) (FIG. 9). Binding was conducted at 37° C. for the following formulations: immunoliposomes having an attached anti-CD19 antibody via a hydrazide linkage (▼), immunoliposomes having an attached anti-CD19 antibody via a PDP linkage (♦), liposomes with an active hydrazide terminus (□), liposomes with an active PDP terminus (△) and conventional liposomes, formed of HSPC-Cholesterol (2:1 molar ratio) (●).

FIG. 9 shows binding to human peripheral blood mononuclear cells of immunoliposomes having an attached anti-CD19 antibody via a hydrazide linkage (■) immunoliposomes having an attached anti-CD19 antibody via a PDP linkage (▲), liposomes with an active hydrazide terminus (□), liposomes with an active PDP terminus (△) and for conventional liposomes formed of HSPC-cholesterol (2:1 molar ratio) (●).

Both the human spleen cells and the peripheral blood mononuclear cells are heterogenous cell populations, as indicated in Table 2 of Example 6. In each case the immunoliposomes having an attached anti-CD19 antibody had a higher binding to a component of the spleen cells and the peripheral blood mononuclear cells.

Cell binding was also analyzed using immunoliposomes and liposomes having a fluorescent marker NBD-PE. Binding was determined by FACS, as described in Example 6C and shown in FIGS. 10A–10G. FIG. 10A shows the fluorescence intensity of the Namalwa cells alone, plotting the relative number of cells as a function of the fluorescence intensity. FIG. 10B shows the fluorescence intensity of anti-CD19 antibody labeled with fluorescein isothiocyanate (FITC). The shift of the peak to the right, that is to higher fluorescence intensity, indicates higher binding. As expected, the CD19+ Namalwa cells bound free anti-CD19 antibody, as seen by comparing FIGS. 10A and 10B. Immunoliposomes having an attached anti-CD19 antibody had a significantly higher binding (FIG. 10C) than liposomes with no antibody (FIG. 10E) or with an attached isotype-matched, non-specific IgG$_{2A}$ antibody (FIG. 10F). The addition of excess free anti-CD19 (unlabeled) antibody to immunoliposomes competitively blocks the binding of the immunoliposomes, as seen in FIG. 10G.

Similar experiments with a heterogenous population of human spleen cells were performed, and the results are shown in FIGS. 11A–11F. A percentage of the human spleen cells have been shown to be CD19+ B cells. Fluorescence activity of the cells alone is shown in FIG. 11A. The shift of a portion of the peak to the right, as seen in FIG. 11B, indicates that free anti-CD19 labeled with FITC bound to a portion of the spleen cell population. Similarly, NBD-PE labeled immunoliposomes having an attached anti-CD19 antibody appear to label the same population of cells, as seen by comparing FIG. 11C with FIG. 11B. This cell population was not labeled by liposomes lacking the attached antibody (FIGS. 11D and 11E) or by immunoliposomes having an attached non-specific IgG$_{2A}$ antibody (FIG. 11F).

The experiments described above with respect to FIGS. 10 and 11 were repeated using H9 cells, i.e., CD4+, CD8-negative, CD19-negative T-cells, with the results shown in FIGS. 12A–12H. The fluorescence intensity for the T cells alone are shown in FIG. 12A. The T-cells could be labeled with free anti-CD4 antibody tagged with phycoerythrin (PhE), however, the cells were not labelled by tagged anti-CD8 or anti-CD19 (FIGS. 12C and 12D). Similarly, no cells were labeled with PEG-free, conventional liposomes (FIG. 12E), or with liposomes (FIG. 12F) or with immunoliposomes having an attached anti-CD19 antibody (FIG. 12G) or with an attached non-specific, isotype-matched IgG$_{2A}$ antibody (FIG. 12H).

Two-color immunofluorescence was used to study binding with peripheral blood mononuclear cells and selective recognition by B-cells was determined using FACScan. Peripheral blood mononuclear cells from multiple myeloma patients were labelled with either NBD-labeled immunoliposomes having an attached anti-CD19 antibody or NBD-labeled liposomes and either anti-CD20-phycoerythrin (PhE), a B-cell marker, or anti-CD4,8-PhE, a T-cell marker. Results are shown in FIGS. 13A–13F where panel A shows the cells alone and panel B shows the cells along with anti-CD19-FITC and anti-CD4,8-PhE, for staining the B and T cells, respectively. As seen in panel A, the cells are grouped at the origin, indicating no red or green staining. In panel B, the B-cells that bind to the green anti-CD19-FITC stain have shifted to the upper left quadrant and the T-cells that stain red with anti-CD4,8-PhE have shifted to the lower right quadrant. Cells that stain both red and green, of which there are relatively few, are located in the upper right quadrant. Panel C shows the cells after exposure to NBD-labeled immunoliposomes with anti-CD19 attached and anti-CD4,8-PhE. The cells seen in the upper left quadrant are the B-cells that bind to the immunoliposomes, with very little labeling to the T-cell population observed (lower right quadrant). In panel D, NBD-labeled immunoliposomes having an attached anti-CD19 antibody and anti-CD20-PhE were added to the cells and the red and green labeling to the B-cells is apparent by the cells present in the upper right quadrant. The T-cells remain near the origin. Panels E and F shows experiments using NBD-labeled liposomes, that is with no attached antibody. In panel E the T-cells respond to the anti-CD4,8-PhE stain and shift to the lower right quadrant, whereas the B-cells are not stained, e.g., no binding to the liposomes, and stay in the lower left quadrant. Panel F shows that the B-cells are stained by the anti-CD20-PhE and not by the liposomes.

In summary, the two-color cytometry experiments indicate that the immunoliposomes having an attached anti-CD19 antibody selectively bind B-cells, with little or no labeling to the T-cell population.

Liposome Internalization

Internalization of liposomes was studied using a pH-sensitive dye, 1-hydroxypyrene-3,6,8-trisulfonic acid (HPTS) encapsulated within the liposomes, as described in Example 7. Table 3 shows the results of the internalization experiments At 4° C., none of the liposome formulations appear to be internalized by the cells, as expected since the mechanism of internalization is known to be inhibited at 4° C. However at 37° C., the immunoliposomes having an attached anti-CD19 antibody are internalized, as evidenced by the decrease in pH to 6.5. After 4 hours, the pH of the cells exposed to the immunoliposomes has decreased to 5.9. The studies indicate that the immunoliposomes appear to be taken up into an acidic compartment within the cells, possibly the lysosomal apparatus.

TABLE 3

| Formulation | pH after treatment with formulation | | |
|---|---|---|---|
| | 4° C., 1 hour | 37° C., 1 hour | 37° C., 4 hours |
| Liposome, no PEG (HSPC:chol) | 7.3 ± 0.1 | 7.2 ± 0.2 | — |
| Liposome (HSPC:chol:mPEG) | 7.4 | 7.3 ± 0.1 | — |
| Immunoliposome (HSPC:chol:mPEG:anti-CD19) | 7.1 ± 0.1 | 6.5 ± 0.3 | 5.9 ± 0.2 |

In vitro Cytotoxicity

Figure 14A:
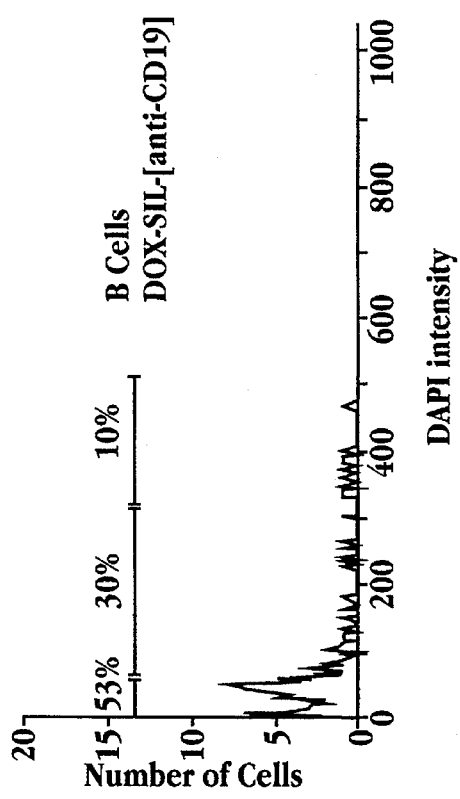
FIGS. 14A–14D show cell cytotoxicity studies using the DAPI assay for cellular DNA content of peripheral blood mononuclear cells, where the DAPI profiles are shown of B cells following treatment with free doxorubicin and with doxorubicin encapsulated in PEG-coated immunoliposomes (A, B) and of T cells following similar treatments (C, D)
Figure 14B:
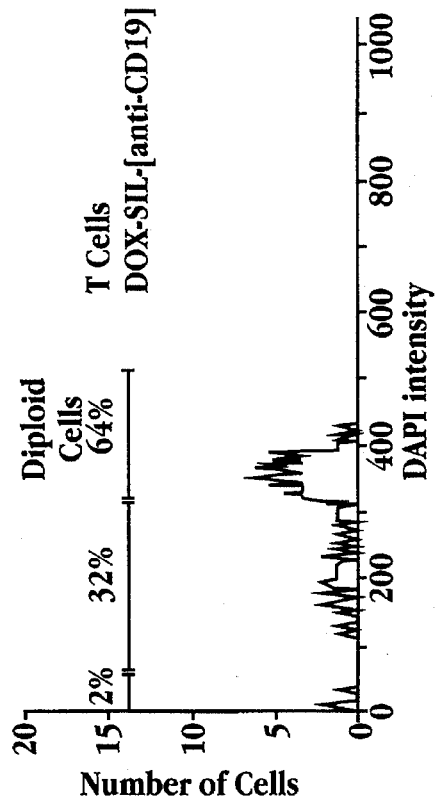
Figure 14C:
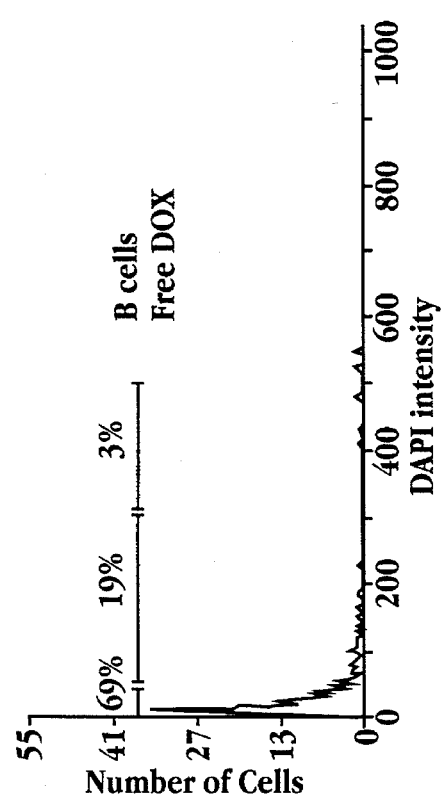
Figure 14D:
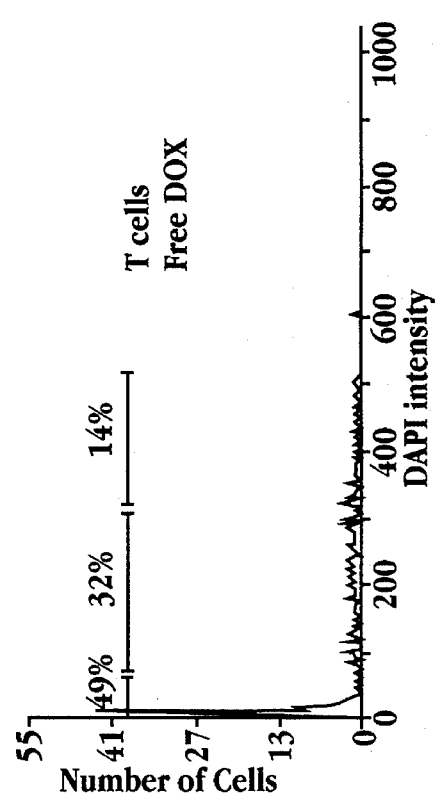

Cytotoxicity experiments were performed using peripheral blood mononuclear cells obtained from multiple myeloma patients. The cells were incubated, as described in Example 8, with free doxorubicin and with immunoliposomal entrapped doxorubicin. Cell populations of B or T cells were selected by appropriate gating and each of the populations was analyzed for DAPI binding. FIGS. 14A–14D show the results and, as seen in FIGS. 14A and 14C, treatment of the cells with 5 µM free doxorubicin kills both the B-cells (FIG. 14A) and the T-cells (FIG. 14C). Doxorubicin entrapped in immunoliposomes having an attached anti-CD19 antibody is selectively cytotoxic to the malignant B-cell (FIG. 14B), sparing the T-cell population (FIG. 14D).

C. In vivo Treatment with Immunoliposomes

In one embodiment of the invention, the above described antibody-liposome composition, containing an anti-tumor compound in liposome-entrapped form, is used for treatment of a plasma cell disorder, such as multiple myeloma. The immunoliposome likely enhances the therapeutic efficacy of the compound by targeting the immunoliposome, and the therapeutic compound, selectively to the affected B-cells.

Experiments in support of the present invention were performed on mice injected intraperitoneally with Namalwa cells, as described in Example 9. After the cells were implanted in vivo, a tumor developed into an ascitic tumor with prominent solid tumors in the lymph nodes and mesenteries. Significantly, in this tumor model, doxorubicin administered parenterally in antibody-liposome entrapped form substantially increased the survival time of mice with the tumor.

Figure 15:
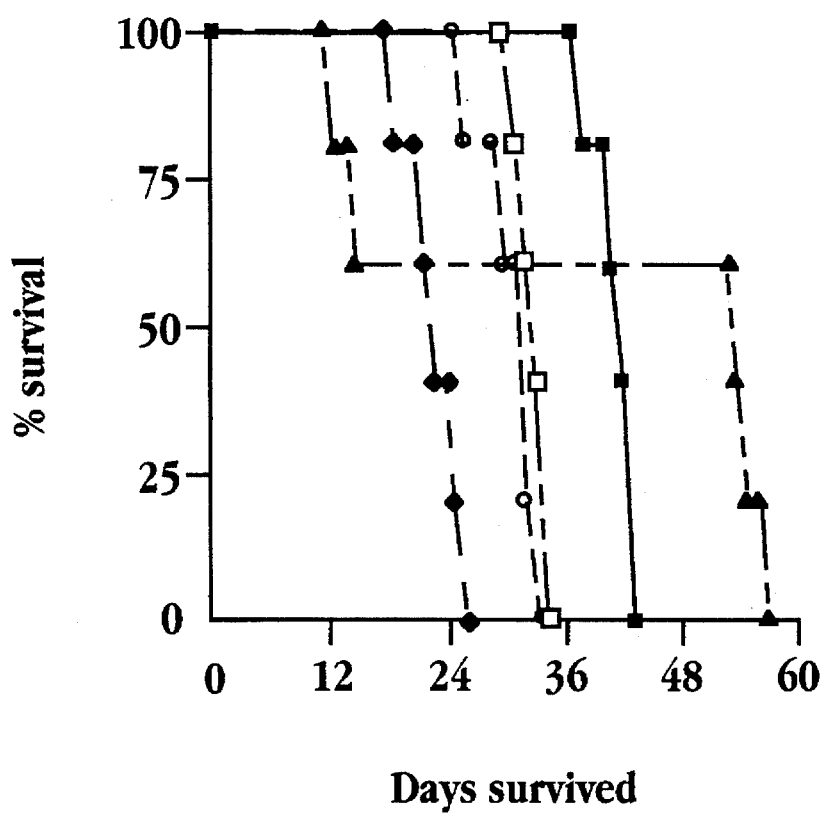
FIG. 15 shows percent survival of mice injected with Namalwa cells as a function of days survived after no treatment (control, △) and after a single dose of 3 mg/kg doxorubicin, administered intraperitoneally in free form (○), entrapped in liposomes (□), entrapped in immunoliposomes administered in a single dose of 3 mg/kg, (■) and entrapped in immunoliposomes administered in a single dose of 6 mg/kg (▲)

FIG. 15 shows survival data for mice injected intraperitoneally with a single injection of saline (control) or a single injection of doxorubicin at a dose of either 3 mg/kg or 6 mg/kg. Doxorubicin was administered at a dose of 3 mg/kg in free form (o), entrapped liposomes (□) and entrapped in immunoliposomes (■), prepared as described in Example 9. A single dose of 6 mg/kg doxorubicin entrapped in immunoliposomes was administered to one group of mice (▲).

FIG. 15 shows that mice, left untreated, have a mean survival time of about 23 days. Treatment with doxorubicin in free form or entrapped in liposomes resulted in similar mean survival times of approximately 31 days. Treatment with doxorubicin entrapped in immunoliposomes having an attached anti-CD19 antibody increased survival time to 41 days at a dose of 3 mg/kg and to 57 days at a dose of 6 mg/kg, a 77% increase and a 137% increase, respectively, in life span over mice left untreated.

Figure 16A:
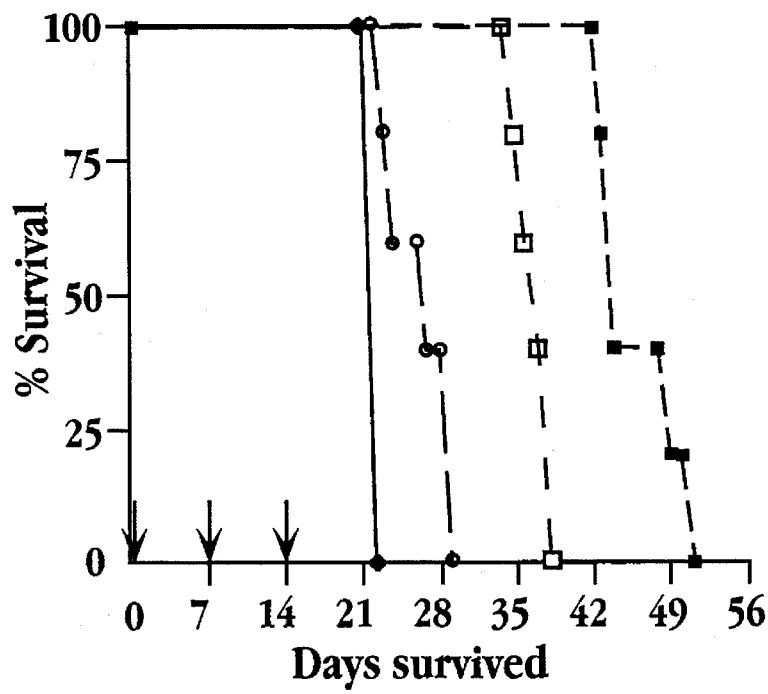
FIG. 16A shows percent survival of mice injected with Namalwa cells as a function of days survived after no treatment (control, ●) and three intraperitoneal injections of 3 mg/kg doxorubicin, administered in free form (○), entrapped in liposomes (□), and entrapped in immunoliposomes (■)
Figure 16B:
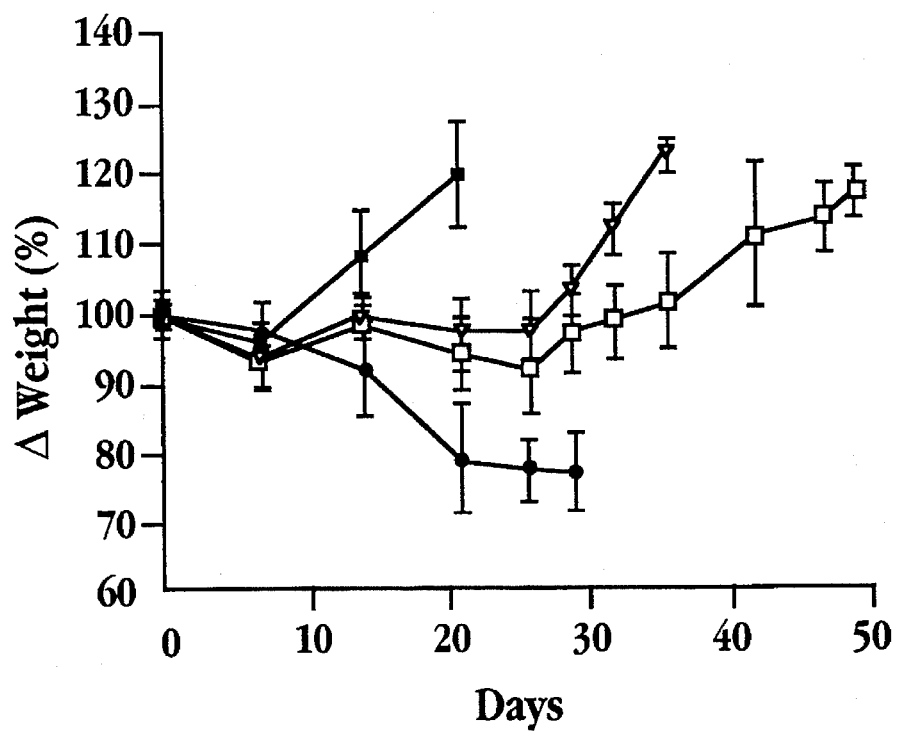
FIG. 16B shows percent weight change as a function of days for the mice described in FIG. 16A, where weight change is shown for mice treated with saline (■), free doxorubicin (●), liposome entrapped doxorubicin (▽), and immunoliposome entrapped doxorubicin (□).

FIGS. 16A–16B show results for a similar experiment, where three intraperitoneal injections of doxorubicin were administered to infected mice. Injections of 3 mg/kg doxorubicin were given at days 1, 7 and 14 post-infection in the following formulations: free form (o), entrapped in liposomes (□), and entrapped in immunoliposomes (■). Percent survival is shown in FIG. 16A, where the control group, treated with saline, are indicated by the (●) symbols. The immunoliposome form of doxorubicin resulted in the longest survival rates, increasing the lifespan 107% over mice left untreated.

FIG. 16B shows percent weight change as a function of time for the mice treated as described in FIG. 16A, where an increase in weight was observed for the control group (■) and the groups treated with liposomes (∇) and immunoliposomes (□). The group treated with free doxorubicin showed a decrease in weight (●), with deaths due to drug toxicities.

V. Examples

The following examples illustrate, but in no way are intended to limit, the present invention.

Materials

Hydrogenated soy phosphatidylcholine (HSPC) was obtained from Asahi Chemicals, Japan. Cholesterol (CH) was purchased from Sigma Chemicals (St. Louis, Mo.).

EXAMPLE 1

Preparation of DSPE-PEG-Maleimide

A. Preparation of the Mono 2-nitrobenzene-sulfonamide of PEG bis(amine) (compound II)

A mixture of 1.7 g (0.5 mmole) of commercially available polyethylene glycol bis(amine) and 104 mg (0.55 mmole) of 2-nitrobenzene sulfonyl chloride were added to a round-bottomed flask. A minimum amount of dioxane to effect solution (about 15 ml) and 280 microliters of triethylamine (2 mmole) were added. The reaction flask was stoppered and allowed to stand at room temperature for 4 days.

Thin layer chromatography (TLC) on silica coated plates using a solvent mixture of the following composition $CHCl_3:CH_3OH:H_2O:NH_4OH$, 130:70:8:0.5 (v/v/v/v), showed fluorescence quenching spots at $R_f$=0.87 to 0.95 and $R_f$=0.68–0.75. The 2-nitro benzene sulfonyl chloride was a more compact spot at $R_f$=0.85. The UV absorbing material at $R_f$=0.87–0.95 was tentatively identified as the bis-2-nitrobenzenesulfenamide. The material at $R_f$=0.68–0.75 was assigned to the desired mono-2-nitro-benzenesulfonamide of the starting diamine.

The solvent was evaporated under vacuum to obtain 2.135 g of a yellow syrup. The crude syrup was dissolved in 5 ml chloroform and placed at the top of a 21 mm×270 mm column of $SiO_2$ wetted with chloroform. The product was purified by passing through the column, in sequence:

| Amount (ml) | Volume % Chloroform | Volume % MeOH containing 1% conc. NH$_4$OH |
|---|---|---|
| 100 | 100% | 0% |
| 200 | 90% | 10% |
| 100 | 80% | 20% |
| 100 | 70% | 30% |

Fifty ml aliquots were collected separately and assayed by TLC as described above. Most of the yellow, ninhydrin positive-reacting material was eluted in the 20% MeOH fraction. The fractions were dried and resulted in recovery of 397 mg of a bright yellow solid. The yield of the pure sample was about 20%.

B. Preparation of the Imidazole Carbamide of the Mono 2-nitrobenzenesulfonamide of PEG bis(amine) (compound III)

550 mg (0.15 mmole) of the 2-nitrobenzenesulfonamide of PEG bis(amine), compound II, were dissolved in anhydrous benzene. To this was added 49 mg of carbonyl diimidazole (0.3 mmole) and 28 microliters (0.20 mmole) of triethylamine. The air in the reaction vessel was displaced with nitrogen, the flask sealed and the reaction mixture was heated in an 80° C. oil bath for 4 hours. TLC on silica-coated plates using the same solvent system as described above showed that all of the starting sulfonamide (Rf=0.72) had been consumed, and had been replaced by an iodine absorbing material at Rf=0.92. The solvent was removed under vacuum. The residue was dissolved in about 2.5 ml chloroform and transferred to the top of a 21×280 mm column of silica which was wetted with chloroform. The following solvents were passed through the column, in sequence:

| Amount (ml) | Volume % Chloroform | Volume % MeOH containing 1% conc. NH$_4$OH |
|---|---|---|
| 100 | 100% | 0% |
| 100 | 90% | 10% |
| 200 | 80% | 20% |

50 ml fractions were collected and assayed by TLC. The desired product, compound III, was found predominantly in the 80–20 chloroform-methanol fractions. Upon evaporating the pooled fractions to dryness, 475 mg of a lemon-yellow solid was obtained (compound III).

C. Preparation of the DSPE carbamide of the 2-nitrobenzene sulfonamide of PEG bis(amine)

To the 450 mg (0.125 mmole) of 2-nitrobenzenesulfonamide of the imidazole carbamide of PEG bis(amine) (compound III) dissolved in 4.5 ml benzene was added 93 mg DSPE (0.125 mmole) and 70 microliters (0.50 mmole) of triethylamine. The reaction flask was then flushed with nitrogen, stoppered, and the contents heated in an oil bath at 80° C. for 6 hours with stirring. The reaction mixture was then cooled to room temperature and analyzed by TLC. TLC indicated that all of the DSPE had been consumed (e.g., the reaction had gone to completion). The solvent was evaporated under vacuum and the residue was dissolved in 2.5 ml chloroform and placed at the top of a 21×260 mm column of silica wetted with chloroform. The sample was purified by passing through the column in sequence:

| Amount (ml) | Volume % Chloroform | Volume % MeOH containing 1% conc. NH$_4$OH |
|---|---|---|
| 100 | 100% | 0% |
| 200 | 90% | 10% |
| 100 | 80% | 20% |
| 100 | 70% | 30% |

The desired product eluted at 20% (1% conc. NH$_4$OH in MeOH), was evaporated and afforded 358 mg of a bright yellow solid with an Rf=0.95. Fractions containing imidazole were not used and the final yield of the product (0.0837 mmoles) was 65%.

D. Preparation of the DSPE Carbamide of PEG bis(amine) (compound IV)

The product from Example 1C above (~358 mg) was dissolved in 10 ml ethanol. To this solution was added 2.4 ml water and 1.2 ml acetic acid. The mixture was allowed to stand at room temperature for 18 hours. TLC analysis after 18 hours indicated that only partial deprotection had occurred. To the reaction mixture was added another 2.3 ml water and 1.2 ml acetic acid and the reaction mixture was then allowed to stir overnight. TLC analysis on silica-coated plates using a similar solvent system as described above revealed florescence quenching materials with R$_f$ values of 0.86 and 0.74, respectively. The desired ninhydrin reactive, phosphate-containing material migrated with an Rf value of 0.637. This spot showed no fluorescence quenching.

The solvent was removed under vacuum. The remaining residue was redissolved in 15 ml chloroform and extracted with 15 ml 5% sodium carbonate. The mixture was centrifuged to effect separation, and the sodium carbonate phase was reextracted 2× with 15 ml chloroform. The combined chloroform extracts were evaporated under reduced pressure to obtain 386 mg of wax. TLC indicated that the wax was largely a ninhydrin positive, phosphate containing lipid of R$_f$=0.72.

The wax was dissolved in 2.5 ml chloroform and placed on a silica column which had been wetted with chloroform. The following solvents were passed through the column in sequence:

| Amount (ml) | Volume % Chloroform | Volume % MeOH containing 1% conc. NH$_4$OH |
|---|---|---|
| 100 | 100% | 0% |
| 200 | 90% | 10% |
| 100 | 80% | 20% |
| 100 | 70% | 30% |
| 100 | 50% | 50% |
| 100 | 0% | 100% |

The samples were assayed by TLC. The desired product was found in fractions containing 70-30 and 50-50 chloroform-methanol as eluent. These samples were combined and evaporated to dryness under vacuum to afford 91 mg (22 micromoles) of a viscous syrup.

E. Preparation of the Maleic Acid Derivative of the DSPE Carbamide of PEG bis(amine) (compound V)

To 18 micromoles of the viscous syrup prepared in Example 1D above and dissolved in 1.8 ml chloroform was added 3.5 mg (36 micromoles) maleic anhydride and 5 microliters (36 micromoles) triethylamine. The stoppered flask containing the reaction mixture was allowed to stand at room temperature for 24 hours and the solvent was subsequently evaporated under reduced pressure. TLC on silica plates indicated that all of the starting material had been replaced by a ninhydrin-negative, phosphate containing material of Rf=0.79–1.00 (Compound V).

F. Preparation of the Maleimide of the DSPE carbamide of PEG bis (amine) (compound VI).

The syrup was dissolved in 2 mls acetic anhydride saturated with anhydrous sodium acetate. The solution was heated in a 50° C. oil bath for two hours. After cooling to room temperature, 10 ml ethanol was added to the contents of the flask and the volatile components were then evaporated under vacuum. This step was repeated twice to remove excess acetic anhydride and acetic acid. The resulting residue was taken up 1 ml chloroform and passed through a silica gel column using the following solvents in sequence:

| Amount (ml) | Volume % Chloroform | Volume % MeOH containing 1% conc. NH$_4$OH |
| --- | --- | --- |
| 100 | 100% | 0% |
| 200 | 90% | 10% |
| 100 | 80% | 20% |
| 100 | 70% | 30% |

50 ml samples were collected and the main product was found in the fractions eluted with 90-10 chloro-form-methanol. The fractions were combined and evaporated to dryness under vacuum to afford 52 mg of a pale yellow viscous oil, which by TLC migrated with an Rf of 0.98 and was determined to contain phosphate. 12.3 micromoles of product (compound VI) were obtained, corresponding to a yield of about 34%.

The synthetic steps described in Example 1A–1F above are illustrated in FIGS. 2A–2B.

EXAMPLE 2

Preparation of DSPE-PEG-Hydrazide (Compound XXXII)

A. Preparation of ω-Hydroxy Acid Derivative of PEG, α-(Hydroxyethyl)-ω-(carboxymethyl-amino-carbonyl)oxy-poly(oxyethylene)Compounds XIX and XXIX)

Polyethylene glycol (Fluka, PEG-2000, 42 g, 42 mequiv OH) is dissolved in toluene (200 ml), azeotropically dried (Zalipsky, et al., 1987) and treated with ethyl isocyanotoacetate (2.3 ml, 21 mmol) and triethylamine (1.5 ml, 10 mmol). The reaction mixture is stirred overnight at 25° C. and the solution is then evaporated to dryness. The residue is dissolved in 0.2M NaOH (100 ml) and any trace of toluene is removed by evaporation. The solution is maintained at pH 12 with periodical dropwise addition of 4M NaOH.

When the solution pH is stabilized at pH 12, the solution is acidified to pH 3.0 and the product is extracted with methylene chloride (100 ml×2). TLC on silica gel (isopropyl alcohol/H$_2$O/conc. ammonia 10:2:1) gives a typical chromatogram of partially carboxylated PEG (Zalipsky, et al., 1990) consisting of unreacted PEG (R$_f$=0.67), monocarboxylated derivative (R$_f$=0.55) and dicarboxylated derivative of the polymer (R$_f$=0.47). This solution is dried over anhydrous MgSO$_4$, filtered and evaporated to dryness. The PEG mixture is dissolved in water (50 ml). One-third of this solution (30 ml ≈14 g of derivatized PEG) is loaded onto DEAE-Sephadex A-25 (115 ml of gel in borate form). After the underivatized PEG is washed off the column with water (confirmed by negative poly(methacrylic acid), PMA, test) (Zalipsky, et al., 1990), a gradient of ammonium bicarbonate (2–20 mM at increments of 1–2 mM every 200 ml) is applied, and 50 ml fractions are collected. Early eluting fractions, e.g., fractions 1–25, typically contain only PEG monoacid as determined by PMA and TLC analyses. These fractions are then pooled, concentrated to ≈70 ml, acidified to pH 2 and extracted with methylene chloride (50 ml×2). The CH$_2$Cl$_2$ solution is dried over anhydrous MgSO$_4$, concentrated and poured into cold stirring ether. The precipitated product (compound XXIX) is dried in vacuo. Yield: 7 g. Titration of carboxyl groups gives 4.6·10$^4$ mequiv/g (97% of theoretical value).

B. Preparation of Compound XXX

Compound XXIX (5 g, 2.38 mmol) and tert-butyl carbazate (0.91 g, 6.9 mmol) are dissolved in CH$_2$Cl$_2$-ethyl acetate (1:1, 7 ml). The solution is cooled on ice and treated with DCC (0.6 g, 2.9 mmol) predissolved in the same solvent mixture. After 30 minutes the ice bath is removed and the reaction is allowed to warm to room temperature and stirred for an additional 3 hours. The reaction mixture is filtered to remove dicyclohexylurea and the resulting filtrate is evaporated to produce a crude residue. The residue is recovered and purified by two precipitations from ethyl acetate-ether (1:1) and dried in vacuo over P$_2$O$_5$. Yield: 5.2 g, 98%. TLC of the product reveals one spot (R$_f$=0.68) with an R$_f$ value different from that of the starting material (R$_f$=0.55). H-NMR (CDCl$_3$): δ1.46 (s, t-Bu, 9H); 3.64 (s, PEG, 178H); 3.93 (br. d, J=4.5, CH$_2$ of Gly, 2H); 4.24 (t, C$\underline{H}_2$—OCO-Gly, 2H) ppm. $^{13}$C-NMR (CDCl$_3$): δ28.1 (t-Bu); 43.4 (CH$_2$ of Gly); 61.6 (CH$_2$OH); 64.3 ($\underline{C}H_2$OCONH); 69.3 ($\underline{C}H_2$CH$_2$OCONH); 70.5 (PEG); 72.4 ($\underline{C}H_2$CH$_2$OH); 81.0 (CMe$_3$); 155.1 (C=O of Boc); 156.4 (C=O of Gly urethane; 168.7 (C=O of Gly hydrazide) ppm.

C. Preparation of Compound XXXI

The ω-hydroxy Boc-hydrazide derivative of PEG (compound XXX, 5 g, 2.26 mmol) is dissolved in pyridine (1.1 ml), CH$_2$Cl$_2$ (5 ml) and CH$_3$CN (2 ml) and treated with disuccinimidyl carbonate, DSC (1.4 g, 5.5 mmol). The reaction mixture is stirred at 25° C. overnight. The mixture is then filtered to remove solids and slowly added to cold ethyl ether (100 ml). The precipitated product is dissolved in warm ethyl acetate (45 ml), chilled and mixed with equal volume of ethyl ether. The precipitate is collected by filtration and dried in vacuo over P$_2$O$_5$. Yield of compound XXXI: 4.8 g, 90%.

Succinimidyl carbonate group content 4.15·10$^{-4}$ mequiv/g (98% of theoretical value) is determined by titration (Zalipsky, et al., 1991). H-NMR (CDCl$_3$): δ1.46 (s, t-Bu, 9H); 2.83 (s, succinimide); 3.64 (s, PEG, 178H); 3.79 (t, C$\underline{H}_2$CH$_2$OCO$_2$-Su); 3.93 (br. d, J=4.5, CH$_2$ of Gly, 2H); 4.24 (t, C$\underline{H}_2$—OCO-Gly, 2H); 4.46 (t, C$\underline{H}_2$OCO$_2$-Su) ppm.

D. Preparation of Compound XXXII

To prepare the DSPE-PEG-hydrazide, a slight excess of succinimidyl carbonate Boc-protected PEG-glycine hydrazide (compound XXXI) is reacted with DSPE suspended in chloroform in the presence of triethylamine. The lipid derivative is quickly (5–10 minutes) solubilized during progress of the reaction. Excess heterobifunctional PEG is removed by dialysis using a 300,000 MWCO cellulose ester dialysis membrane from Spectrum. The recovered lipid conjugate is subjected to conventional Boc-deprotection conditions (4M HCl in dioxane for 30 minutes) and then further purified by recrystallization. H-NMR (CDCl$_3$): δ0.88 (t, CH$_3$, 6H); 1.59 (t, C$\underline{H}_2$CH$_2$CO, 4H); 2.84 (t, CH$_2$CO, 4H); 3.64 (s, PEG, 180H); 4.0 (t); 4.2 (m, CH$_2$OCO—NH$_2$); 4.4–4.3 (two doublets); 5.2 (g, CH of glyceride).

Figure 3B:
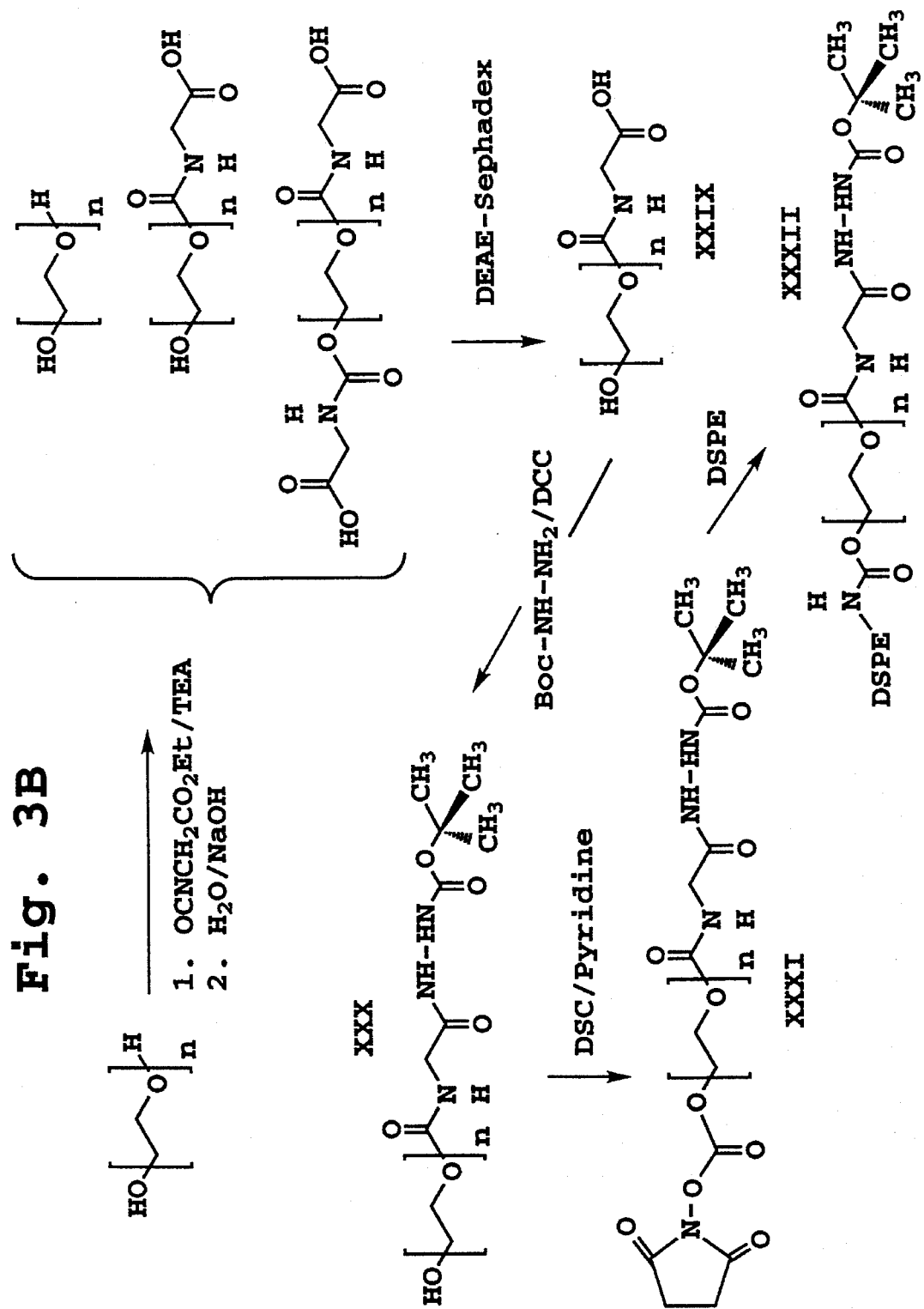
FIG. 3B shows one synthetic approach for forming DSPE derivatized with a PEG spacer chain having a terminal hydrazide group (shown in protected form)

The above synthesis is summarized in FIG. 3B.

EXAMPLE 3

Preparation DSPE-PEG 3-(2-pyridyldithio) propionamide

The DSPE carbamide of PEG his (amine) (compound IV, 50 micromoles) is dissolved in 3 ml of anhydrous methanol containing 50 micromoles of triethylamine and 25 mg of N-succinimidyl 3-(2-pyridyldithio) propionate (SPDP, Pierce, Rockford, Ill.). The reaction is carried out at room temperature for 5 hours under an argon atmosphere. Methanol is removed under reduced pressure, and the products are redissolved in chloroform and applied to a 10 ml silica gel column, using silica gel which has been previously activated at 150° C. overnight. A similar solvent system as described in Example 1 is used to purify the product. Analysis on TLC plates indicates a product (compound VIII) with an $R_f=0.98$ which reacts negatively with ninhydrin, contains phosphate and has no free sulfhydryl groups. When the product is treated with excess dithiothreitol, 2-thio-pyridinone is released.

This synthetic scheme is summarized in FIG. 4.

EXAMPLE 4

Antibody Coupling to DSPE-PEG-Hz

A 10 mg/ml solution of antibody was prepared in 100 mM sodium acetate 70 mM NaCl pH 5.5. For 1 ml of protein solution, 55 microliters of 0.2M sodium periodate was added. Oxidation proceeded for 1 hour at room temperature. The oxidized antibody molecules containing reactive aldehyde groups were added to liposomes containing DSPE-PEG-Hz (prepared as described above) at an antibody:phospholipid molar ratio of 1:1000 and incubated overnight at 25° C. Immunoliposomes were separated from free protein by chromatography on Sepharose CL-4B in TES buffered saline, pH 7.4.

Figure 5:
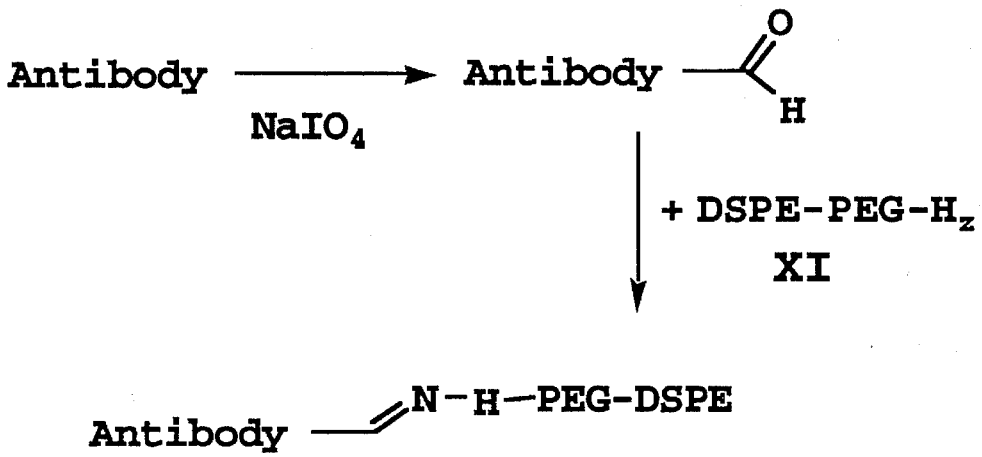
FIG. 5 shows one exemplary method for coupling an antibody containing terminal hydroxy groups to a liposome-attached polyethylene glycol chain having a reactive hydrazide group at its free end.

The above coupling chemistry is summarized in FIG. 5.

EXAMPLE 5

Biodistribution of Immunoliposomes

The biodistribution and blood circulation lifetime of liposomes containing surface-bound antibodies (immunoliposomes) was compared to that of liposomes lacking surface-bound antibodies (liposomes). The immunoliposomes were composed of HSPC:CH:PEG hydrazide, at 2:1:0.1 molar ratio and sheep IgG covalently linked to the free end of a portion of the PEG chains. Liposomes lacking surface-bound antigens were liposomes composed of HSPC:CH:PEG at a 2:1:0.1 molar ratio and liposomes composed of HSPC:CH:PEG hydrazide. The average diameter of the liposomes was between 110 and 120 nanometers. For biodistribution studies the liposomes contained $^{125}$I-tyraminylinulin in liposome-entrapped form (Example 5B). For blood circulation lifetime studies the liposomes contained $^{67}$Gallium in liposome-entrapped form.

The immunoliposomes were prepared as described. A 10 mg/ml solution of IgG was prepared in 100 mM sodium acetate, 70 mM NaCl pH 5.5. For 1 ml of the protein solution, 55 microliters of 0.2M sodium periodate was added. Oxidation proceeded for 1 hour at room temperature. The periodate-treated protein was added to liposomes containing DSPE-PEG hydrazide and incubated overnight at 4° C. Liposomes were separated from free protein by chromatography on Sepharose CL-4B in TES-buffered saline, pH 7.4.

A. Tissue Biodistribution

Female CD(ICR) BR (outbred) mice in the weight range of 23–30 grams were obtained from Charles River Canada (St. Constant, QUE), and maintained in standard housing. Mice (three per group) were given a single bolus injection with 0.2 ml of liposomes containing approximately $10^6$ $_{125}$I-Tl cpm and 0.5 micromole phospholipid, and approximately 10 micrograms antibody, where applicable. Some groups of mice received injection of free radiolabelled TL. Injections were performed by intravenous injection via the tail vein. After specified periods of time, animals were anesthetized with halothane (M.T.C. Pharmaceutical, Ontario) and sacrificed by cervical dislocation. Samples of blood (0.1 ml) and internal organs (liver, spleen, lung, heart, and carcass, which was the remainder of the animal) were collected, tissues were washed and blotted dry to remove superficial blood and counted for label in a Beckman 8000 gamma counter. Blood correction factors, having previously been determined from $^{111}$In-labelled red blood cells (Allen, 1989a), were applied to tissue and carcass.

Data is presented as % of in vivo cpm, which represents the % of counts remaining in the body at a given time point. This corrects for leakage of the label from the liposomes and represents intact liposomes remaining in the body.

TABLE 1

| Liposome Composition (time post-injection) | % of in vivo cpm | | | | | |
|---|---|---|---|---|---|---|
| | Blood | Liver | Spleen | Lung | Heart | Carcass |
| 2 hours | | | | | | |
| HSPC:CH:PEG | 78.1 ± 4.4 | 6.3 ± 0.6 | 2.5 ± 0.4 | 0.1 ± 0.1 | 0.3 ± 0.1 | 11.1 ± 3.8 |
| HSPC:CH:PEG—HZ | 65.6 ± 5.7 | 12.2 ± 1.9 | 1.6 ± 0.2 | 0.4 ± 0.2 | 0.3 ± 0.1 | 18.6 ± 4.2 |
| HSPC:CH:PEG—HZ:IgG | 73.2 ± 6.3 | 10.9 ± 4.4 | 1.0 ± 0.5 | 0.5 ± 0.1 | 0.3 ± 0.1 | 13.0 ± 4.0 |
| 24 hours | | | | | | |
| HSPC:CH:PEG | 26.7 ± 1.1 | 26.4 ± 2.9 | 5.1 ± 0.5 | 0.4 ± 0.1 | 0.5 ± 0.0 | 38.3 ± 2.2 |
| HSPC:CH:PEG—HZ | 14.0 ± 2.3 | 34.8 ± 2.1 | 3.8 ± 0.8 | 0.4 ± 0.2 | 0.4 ± 0.0 | 42.4 ± 4.5 |
| HSPC:CH:PEG—HZ:IgG | 23.1 ± 3.3 | 27.5 ± 4.2 | 3.4 ± 0.5 | 0.3 ± 0.1 | 0.3 ± 0.1 | 38.7 ± 1.8 |

As shown in Table 1 the biodistribution of immunoliposomes are very similar to those of liposomes containing nonfunctionalized PEG chains. Immunoliposome and liposome biodistributions were determined for the blood, liver, spleen, lung, heart and carcass.

B. Blood Circulation Time

A catheter was established in a femoral vein of laboratory rats, 200–300 g each, for removal of blood samples at defined times after injection of immunoliposome and liposome samples, prepared as described above with and without bound antibodies, and containing entrapped $^{67}$Gallium. Radioactivity was measured in the blood samples using a gamma counter and the percent of the injected dose remaining in the blood at 0.5, 1, 2, 4, and 24 hours after iv administration of the two samples was determined. Results are shown in FIG. 6, and it can be seen that both formulations give good blood circulation lifetime, with more than 10% of the injected marker being retained in the bloodstream after 24 hours.

EXAMPLE 6

In vitro Binding Studies

In vitro binding experiments were done with the cell lines shown in Table 2.

TABLE 2

| Cell Line | Cell Type | Antibody |
|---|---|---|
| Namalwa | CD19+, human B lymphoma | anti-CD19 (IgG$_{2A}$) |
| H9 | CD4+, CD8−, CD19− human T lymphoma | anti-CD4 |
| Human spleen cells | heterogenous cell population (e.g., B-cells, T-cells) | anti-CD19 |
| peripheral blood mononuclear cells (PBMC) | heterogenous cell population, CD19, 20+ B-cells, CD4, 8+ T-cells | anti-CD19, anti-CD20, anti-CD4, anti-CD8 |

A. Liposome Preparation

Liposomes were composed of HSPC:cholesterol in a 2:1 molar ratio, along with 5 mol % PEG(2000)-DSPE and 5 mol % DSPE-PEG-Hz. Liposomes were sized to between 95–115 nm in diameter. Fluorescent liposomes contained 1 mol % NBD-PE. Radiolabeled liposomes contained $^3$H-cholesterol hexadecyl ether (CHE). Antibodies were conjugated to the liposomes by the method described in Example 4.

B. In vitro Binding: $^3$H-CHE labeled immunoliposomes

Binding experiments were done with the CD19+ human B-cell lymphoma cell line (Namalwa), T-cell lymphoma cell line (H9 cells), human spleen cells or peripheral blood mononuclear cells obtained from multiple myeloma patients. The binding of various liposomal and immunoliposomal formulations, labeled with $^3$H-CHE, by 10$^6$ cells was determined after 1 hour incubation at 4° C. or 37° C. FIGS. 7A–7B show the binding of immunoliposomes having an attached anti-CD19 antibody, (■), liposomes (□), and immunoliposomes plus excess free anti-CD19 antibody (▼) by CD19+ Namalwa cells at 37° C. (FIG. 7A) and at 4° C. (FIG. 7B). FIG. 7C shows binding by CD19-negative T-cells. Binding is expressed as nmoles liposome phospholipid per 10$_6$ cells as a function of liposome phospholipid concentration, in nmoles/ml.

FIGS. 8 and 9 are plots similar to FIG. 7, showing binding to human spleen cells (FIG. 8) and to peripheral blood mononuclear cells (FIG. 9). Binding was conducted at 37° C. for the following formulations: immunoliposomes having an attached anti-CD19 antibody via a hydrazide linkage (▼), immunoliposomes having an attached anti-CD19 antibody via a PDP linkage (♦), liposomes with an active hydrazide terminus (□), liposomes with an active PDP terminus (△) and for conventional liposomes, formed of HSPC-Cholesterol (2:1 molar ratio) (●).

FIG. 9 shows liposome binding in human peripheral blood mononuclear cells of immunoliposomes having an attached anti-CD19 antibody via a hydrazide linkage (■), immunoliposomes having an attached anti-CD19 antibody via a PDP linkage (▲), liposomes with an active hydrazide terminus (□), liposomes with an active PDP terminus (△) and for conventional liposomes formed of HSPC-cholesterol (2:1 molar ratio) (●).

C. In vitro Binding: fluorescent Activated Cell Sorting (FACS)

Liposomes were prepared with the fluorescent marker NBD-PE and binding was determined by FACS. 1×10$^6$ cells were plated with RPMI containing 10% FBS and incubated with a specific formulation (immunoliposomes, liposomes, free antibody) at 37° C. for 1 hour. Post incubation, cells were washed with PBS and appropriately stained by the immunofluorescent staining protocol. Scans using free antibodies were done using antibodies labeled with fluorescein isothiocyanate (FITC) of phycoerythrin (PhE).

FIGS. 10A–10G show binding with Namalwa cells, plotting the relative number of cells as a function of the fluorescence intensity for the cells alone (A), free anti-CD19-FITC antibody (B), immunoliposomes with attached anti-CD19 antibody (C), conventional liposomes formed of HSPC-cholesterol (D), liposomes (E), immunoliposomes with an attached non-specific IgG$_{2A}$ antibody (F) and excess free anti-CD19 antibody followed by immunoliposomes with attached anti-CD19 antibody (G).

FIGS. 11A–11F shows FACS analyses for the association of fluorescent-labelled liposomes with human spleen cells, plotting the relative number of cells as a function of the fluorescence intensity for the cells alone (A), free anti-CD19 antibody (B), immunoliposomes with attached anti-CD19 antibody (C), conventional liposomes formed of HSPC-cholesterol (D), liposomes (E) and immunoliposomes with an attached IgG$_{2A}$ antibody (F).

FIGS. 12A–12H show FACS analyses for the association of fluorescent-labelled liposomes with CD19-negative T cells, plotting the relative number of cells as a function of the fluorescence intensity for the T cells alone (A), free anti-CD4-PhE antibody (B), anti-CD8-PhE antibody (C), free anti-CD19 -FITC antibody (D), conventional liposomes formed of HSPC-cholesterol (E), liposomes (F), immunoliposomes with attached anti-CD19 antibody (G) and immunoliposomes with an attached isotype matched, non-specific IgG$_{2A}$ antibody (H).

D. In vitro Binding: Two Color Flow Cytometry

Two-color immunofluorescence was used to study binding with peripheral blood mononuclear cells Selective recognition by B-cells was determined using FACScan. Peripheral blood mononuclear cells from multiple myeloma patients were labelled with either NBD-labeled immunoliposomes having an attached anti-CD19 antibody or NBD-labeled liposomes and either anti-CD20-phycoerythrin (PhE), a B-cell marker, or anti-CD4,8-PhE, a T-cell marker. Results are shown in FIGS. 13A–13F.

EXAMPLE 7

Immunoliposome Internalization

Internalization of liposomes was studied using a pH-sensitive dye, 1-hydroxypyrene-3,6,8-trisulfonic acid (HPTS) encapsulated within the following liposome formulations: HSPC-cholesterol, HSPC-cholesterol-DSPE-mPEG, and HSPC-cholesterol-DSPE-mPEG-anti-CD19. Namalwa cells were plated in 48 well plates (1×10$^6$ cells/ well) and HPTS-encapsulated liposomes were incubated at 4° C. and 37° C. with the cells for 1 hour and 4 hours. Cells were washed with PBS and the excitation spectra scanned from λ=320–500 nm keeping the emission wavelength fixed at λ=510 nm. Measuring the ratio of the excitation peaks, 403/413 nm and 450/413 nm, the pH environment of the cells was determined. The results are shown in Table 3.

EXAMPLE 8

Cytotoxicity Studies

Peripheral blood mononuclear cells obtained from multiple myeloma patients were incubated for 24 hours at 37° C. with free doxorubicin and with immunoliposome-entrapped doxorubicin. After incubation, cells were washed in PBS and stained with both anti-CD19-FITC (green) and anti-CD4,8-PhE (red). Ethanol-permeabilized cells, including chicken red blood cells as an internal standard, were stained for DNA content with 4,6-diamino phenylindole (DAPI). Samples were then analyzed on an Elite flow cytometer. Gates were set on the anti-CD19-FITC and the anti-CD4,8-PhE cell populations and 5,000–10,000 events were collected for each run. Files were collected and then analyzed for DAPI binding in each of the cell subtypes. Results are shown in FIGS. 14A–14D.

FIGS. 14A–14D show cell cytotoxicity studies using the DAPI assay for cellular DNA content of peripheral blood mononuciear cells, where the DAPI profiles are shown of B cells following treatment with 5 µM doxorubicin in free form and encapsulated in immunoliposomes (A, B). Profiles of T cells following similar treatments are shown in (C, D).

EXAMPLE 9

In Vivo Survival Experiments

Liposomes were 100 nm in diameter and anti-CD19 antibodies were coupled to the liposomes using DSPE-PEG-Hz, as described in Example 4.

SCID mice (5 mice/group) were injected (i.p.) with 5×10⁷ Namalwa cells. At 24 hours post-implantation of the cells, mice were injected intraperitoneally with a single injection of saline (control) or a single injection of 3 mg/kg free doxorubicin, 3 mg/kg of doxorubicin entrapped in HSPC-:chol:PEG-DSPE liposomes, 3 mg/kg of doxorubicin entrapped in HSPC:chol:PEG-DSPE:DSPE-PEG-Hz-anti-CD19 immunoliposomes, and 6 mg/kg of doxorubicin entrapped in HSPC:chol:PEG-DSPE:DSPE-PEG-Hz-anti-CD19 immunoliposomes.

FIG. 15 shows percent survival as a function of days survived following treatment with saline (Δ), 3 mg/kg doxorubicin, administered intraperitoneally in free form (o), entrapped in liposomes (□), entrapped in immunoliposomes administered in a single dose of 3 mg/kg (■), and entrapped in immunoliposomes administered in a single dose of 6 mg/kg (▲).

In another experiment, mice were injected with Namalwa cells as described above. Post-infection, the mice were treated with three injections, administered intraperitoneally at days 1, 7 and 14, of 3 mg/kg doxorubicin in the following formulations: free form (o), entrapped in liposomes (□), and entrapped in immunoliposomes (■). The results are shown in FIG. 16A, where the control group, treated with saline, are shown by the (●) symbols. FIG. 16B shows percent weight change as a function of time for these mice.

Although the invention has been described with respect to particular embodiments, it will be apparent to those skilled in the art that various changes and modifications can be made without departing from the invention.

It is claimed:

1. A method of treating a subject having a disorder characterized by a neoplasm of B-lymphocyte lineage cells or T-lymphocyte lineage cells, comprising administering to the subject, a suspension of liposomes having a surface coating of polyethylene glycol chains effective to increase the blood circulation lifetime of the liposomes severalfold over that of liposomes in the absence of such coating, a chemotherapeutic agent in liposome-entrapped form, and covalently attached to the distal ends of a portion of said chains, antibodies or antibody fragments effective to bind to an antigen specific for said cells.

2. The method of claim 1, wherein said administering includes administration of liposomes having an attached antibody selected from the group consisting of anti-CD19, anti-CD20 and anti-CD22, for binding to a B-cell antigen.

3. The method of claim 2, wherein said administering includes administration of liposomes having an attached anti-CD19 antibody, and said disorder is multiple myeloma.

4. The method of claim 2, wherein said administering includes administration of liposomes having an attached anti-CD19 antibody, and said disorder is acute lymphocytic leukemia.

5. The method of claim 2, wherein said administering includes administration of liposomes having an attached anti-CD19 antibody, and said disorder is a B-cell lymphoma.

6. The method of claim 2, wherein said administering includes administration of liposomes having an attached anti-CD20 antibody, and said disorder is multiple myeloma.

7. The method of claim 2, wherein said administering includes administration of liposomes having an attached anti-CD20 antibody, and said disorder is acute lymphocytic leukemia.

8. The method of claim 2, wherein said administering includes administration of liposomes having an attached anti-CD20 antibody, and said disorder is a B-cell lymphoma.

9. The method of claim 2, wherein said administering includes administration of liposomes having an attached anti-CD22 antibody, and said disorder is multiple myeloma.

10. The method of claim 2, wherein said administering includes administration of liposomes having an attached anti-CD22 antibody, and said disorder is acute lymphocytic leukemia.

11. The method of claim 2, wherein said administering includes administration of liposomes having an attached anti-CD22 antibody, and said disorder is a B-cell lymphoma.

12. The method of claim 2, wherein said administering includes administration to a subject having multiple myeloma, and said cells are multidrug resistant.

13. The method of claim 1, wherein said administering includes administration of liposomes having an attached antibody selected from the group consisting of anti-CD4 and anti-CD8, for binding to a T-cell antigen.

14. The method of claim 13, wherein said administering includes administration of liposomes having an attached anti-CD4 antibody, and said disorder is a T-cell lymphoma.

15. The method of claim 13, wherein said administering includes administration of liposomes having an attached anti-CD4 antibody and said disorder is acute lymphocytic leukemia.

16. The method of claim 1, wherein said administering includes administration of liposomes having a coating of polyethylene glycol having a molecular weight of between about 500–10,000 daltons.

17. The method of claim 1, wherein said administering includes administration of liposomes having a coating of polyethylene glycol having a molecular weight of between about 500–2,000 daltons.

18. The method of claim 1, wherein said administering includes administration of liposomes having doxorubicin in liposome entrapped form.

19. The method of claim 1, wherein said administering includes administration of liposomes having vincristine in liposome entrapped form.

* * * * *